US012672884B2

(12) United States Patent
Schwartz et al.

(10) Patent No.: US 12,672,884 B2
(45) Date of Patent: Jul. 7, 2026

(54) TOE IMPLANT ASSEMBLIES, KITS, SURGICAL METHODS, AND METHODS OF MANUFACTURING

(71) Applicant: BIOPOLY, LLC, Fort Wayne, IN (US)

(72) Inventors: Herbert E. Schwartz, Fort Wayne, IN (US); Stone P. Miguel, Fort Wayne, IN (US)

(73) Assignee: BioPoly, LLC, Fort Wayne, IN (US)

( * ) Notice: Subject to any disclaimer, the term of this patent is extended or adjusted under 35 U.S.C. 154(b) by 75 days.

(21) Appl. No.: 18/462,145

(22) Filed: Sep. 6, 2023

(65) Prior Publication Data

US 2023/0414230 A1 Dec. 28, 2023

Related U.S. Application Data

(63) Continuation of application No. PCT/US2022/019334, filed on Mar. 8, 2022.
(Continued)

(51) Int. Cl.
*A61B 17/16* (2006.01)
*A61F 2/42* (2006.01)
*A61F 2/46* (2006.01)

(52) U.S. Cl.
CPC ........ *A61B 17/1682* (2013.01); *A61F 2/4225* (2013.01); *A61F 2/46* (2013.01);
(Continued)

(58) Field of Classification Search
CPC ................. A61B 17/864; A61F 2/4241; A61F 2002/4243; A61F 2002/4251; A61F 2002/4253; A61F 2002/4658
(Continued)

(56) References Cited

U.S. PATENT DOCUMENTS

| | | | |
|---|---|---|---|
| 5,037,440 A | | 8/1991 | Koenig |
| 5,370,697 A | * | 12/1994 | Baumgartner ........ A61F 2/4637 |
| | | | 623/17.15 |

(Continued)

FOREIGN PATENT DOCUMENTS

| | | |
|---|---|---|
| AU | 2004201647 | 2/2005 |
| WO | 2020114252 A1 | 6/2020 |

OTHER PUBLICATIONS

International Search Report and Written Opinion of the International Searching Authority for International Application No. PCT/US2022/019334 mailed on Aug. 17, 2022,, 10 pages.
(Continued)

*Primary Examiner* — Matthew J Lawson
(74) *Attorney, Agent, or Firm* — Heslin Rothenberg Farley & Mesiti P.C.

(57) ABSTRACT

A toe implant assembly includes a bearing member having a curved interface surface, and a fixation member having a platform portion and fixation portion. The platform portion has a peripheral portion sized less than or equal to a peripheral portion of the bearing member. The bearing member extends outwardly from the peripheral portion of the platform portion. A kit may include a plurality of differently sized sizing devices, at least one cannulated drill, and a plurality of correspondingly sized trialing devices having a bearing member and fixation member, the bearing member having a curved interface surface having a first diameter, and the fixation member is coupled to the bearing member. The fixation member has a platform having a peripheral diameter less than or equal to the diameter of the peripheral diameter of the bearing member. A surgical method includes using the kit to install a selected toe implant assembly.

14 Claims, 28 Drawing Sheets

Related U.S. Application Data

(60) Provisional application No. 63/158,405, filed on Mar. 9, 2021.

(52) U.S. Cl.
CPC .... *A61F 2/4606* (2013.01); *A61F 2002/4233* (2013.01); *A61F 2002/4631* (2013.01)

(58) Field of Classification Search
USPC ........................................... 623/17.11–17.16
See application file for complete search history.

(56) References Cited

U.S. PATENT DOCUMENTS

| | | | | |
|---|---|---|---|---|
| 5,702,469 | A * | 12/1997 | Whipple | A61F 2/4241 623/21.15 |
| 7,060,097 | B2 * | 6/2006 | Fraser | A61F 2/442 623/17.13 |
| 7,713,305 | B2 * | 5/2010 | Ek | A61F 2/3859 623/20.14 |
| 8,652,211 | B1 * | 2/2014 | Jerry, Jr. | A61F 2/4225 623/21.19 |
| 9,820,861 | B2 * | 11/2017 | Smith | A61B 17/1735 |
| 9,931,219 | B2 * | 4/2018 | Sikora | A61F 2/4618 |
| 10,617,528 | B2 * | 4/2020 | Lauf | A61F 2/4225 |
| 2002/0111680 | A1 * | 8/2002 | Michelson | A61F 2/4465 623/17.11 |
| 2004/0225367 | A1 * | 11/2004 | Glien | A61F 2/3603 623/23.26 |
| 2006/0111726 | A1 | 5/2006 | Felt et al. | |
| 2006/0247787 | A1 | 11/2006 | Rydell et al. | |
| 2007/0038219 | A1 * | 2/2007 | Matthis | A61B 17/8625 623/17.11 |
| 2007/0055380 | A1 * | 3/2007 | Berelsman | A61F 2/4612 623/908 |
| 2008/0097455 | A1 | 4/2008 | Wright et al. | |
| 2009/0105835 | A1 * | 4/2009 | Hovda | A61F 2/4465 623/17.11 |
| 2011/0184527 | A1 * | 7/2011 | Vanasse | A61F 2/42 623/21.15 |
| 2012/0116513 | A1 * | 5/2012 | Carpenter | A61F 2/4611 623/17.16 |
| 2012/0259419 | A1 * | 10/2012 | Brown | A61B 17/1682 623/21.19 |
| 2014/0039621 | A1 | 2/2014 | Gordon et al. | |
| 2018/0153697 | A1 * | 6/2018 | Vitale | A61B 17/1682 |
| 2020/0078185 | A1 | 3/2020 | Marks et al. | |
| 2020/0107937 | A1 * | 4/2020 | Denham | A61F 2/4606 |
| 2020/0138485 | A1 * | 5/2020 | Kuwamura | A61B 17/8685 |
| 2021/0059829 | A1 | 3/2021 | Montross et al. | |
| 2024/0024113 | A1 * | 1/2024 | Torbati | A61F 2/30756 |

OTHER PUBLICATIONS

Schwartz et al., Extended European Search Report and Opinion for European Patent Application No. 22767799.4, dated Jan. 24, 2025, 8 pages, Jan. 24, 2025.

International Preliminary Report on Patentability for International Application No. PCT/US2022/019334, dated Sep. 12, 2023, 7 pages.

* cited by examiner 14 mm    16 mm    18 mm    20 mm    22 mm

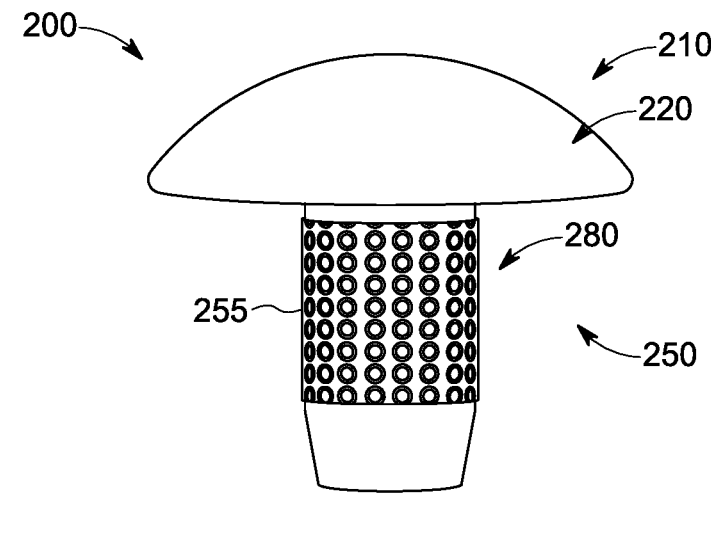
FIG. 11
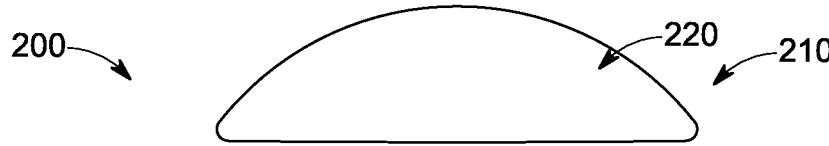
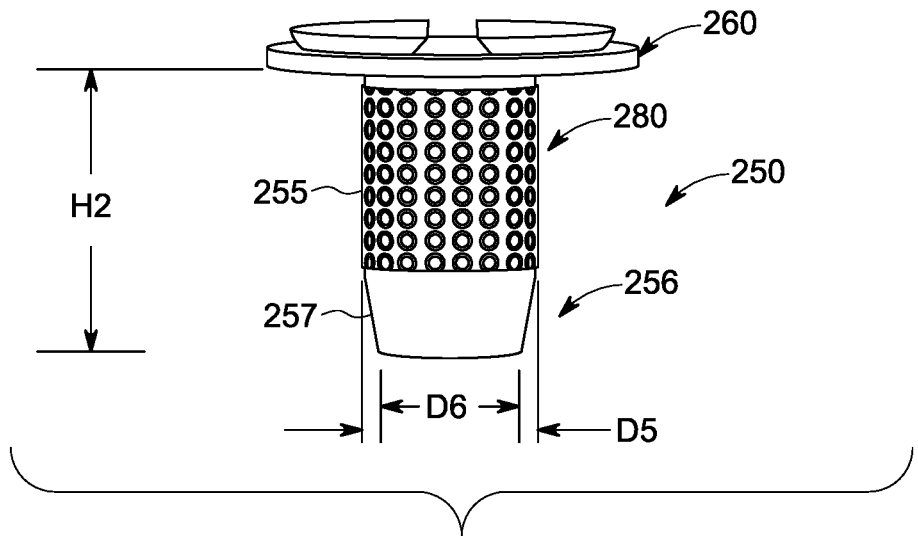
FIG. 12

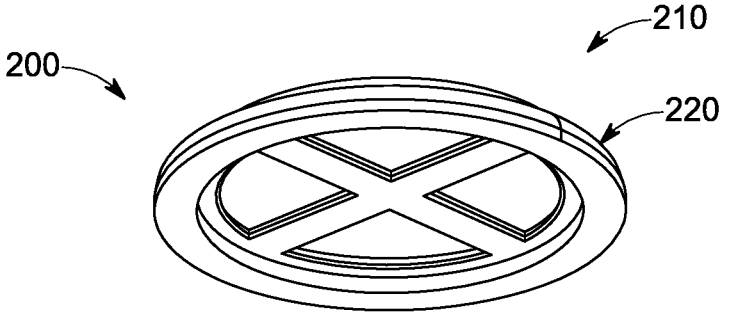
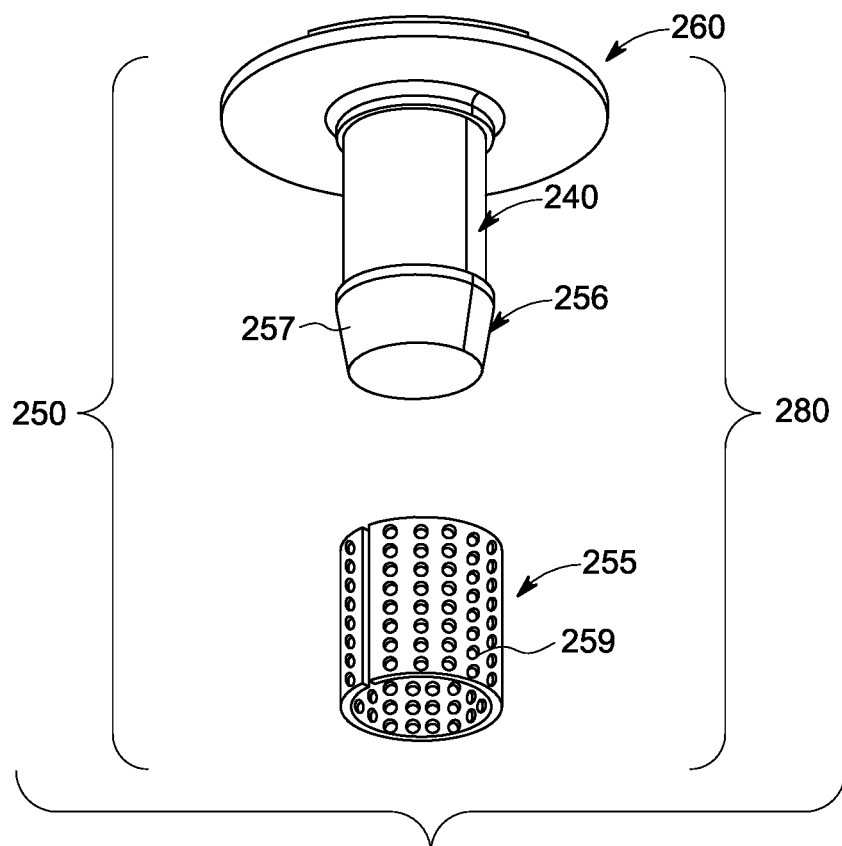
FIG. 13

14 mm        16 mm        18 mm        20 mm        22 mm

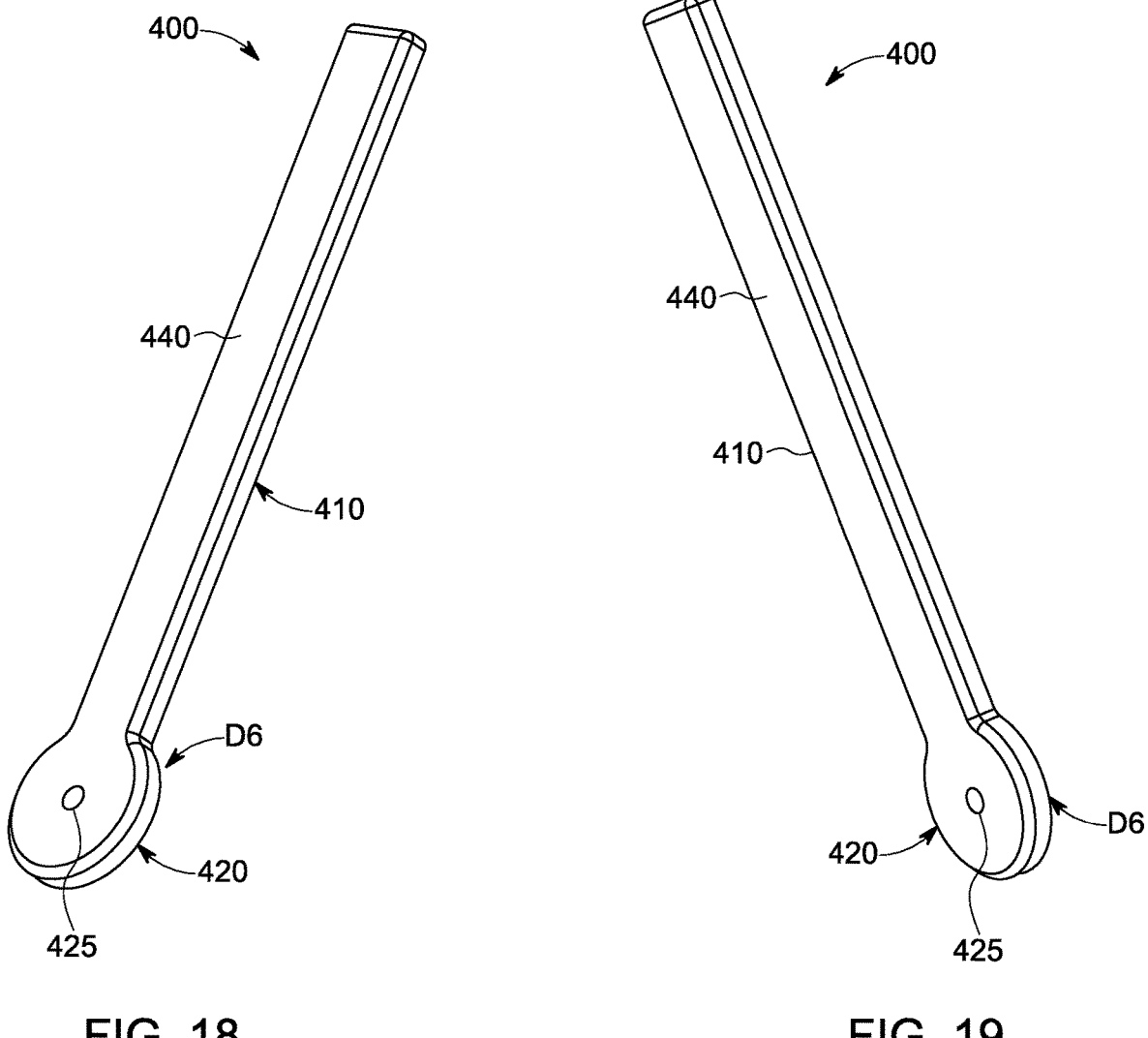
FIG. 18                    FIG. 19

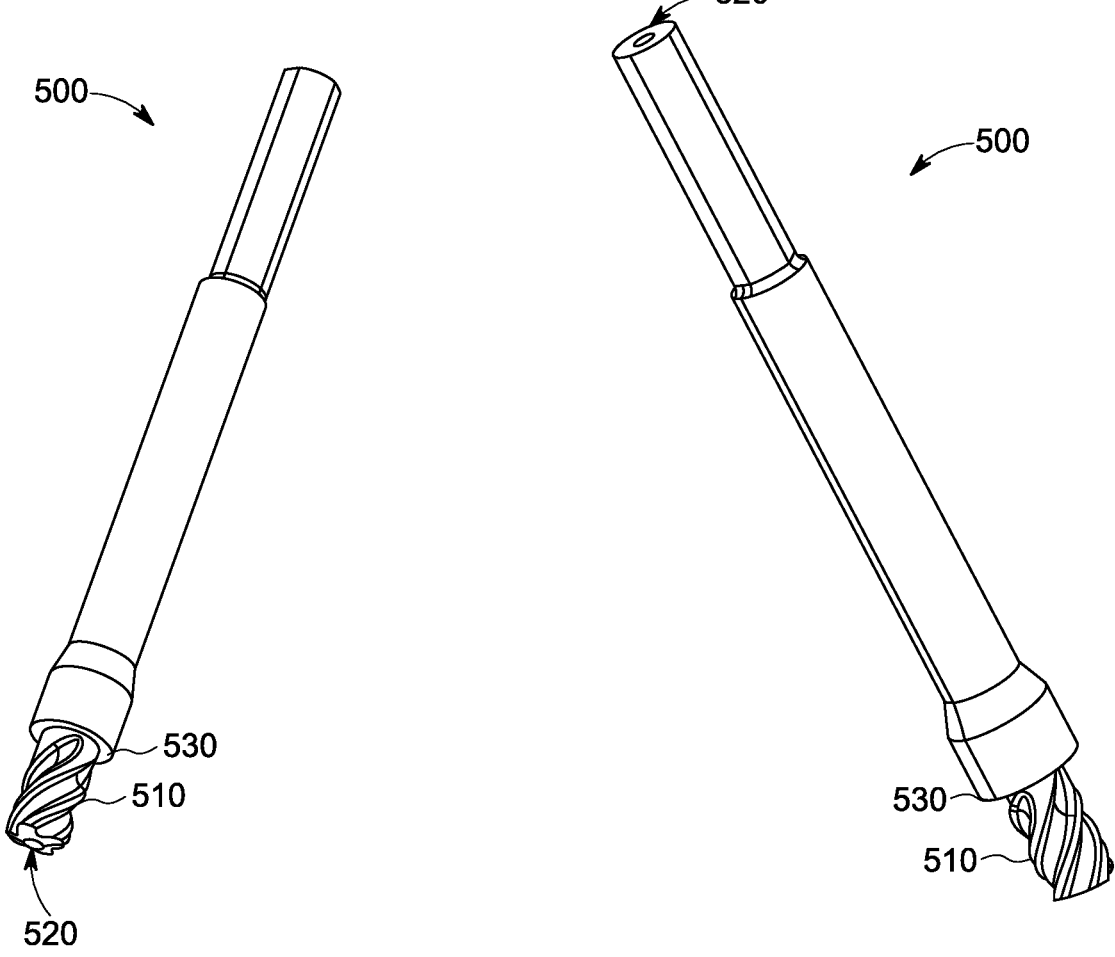
FIG. 20                                    FIG. 21

700

712

715

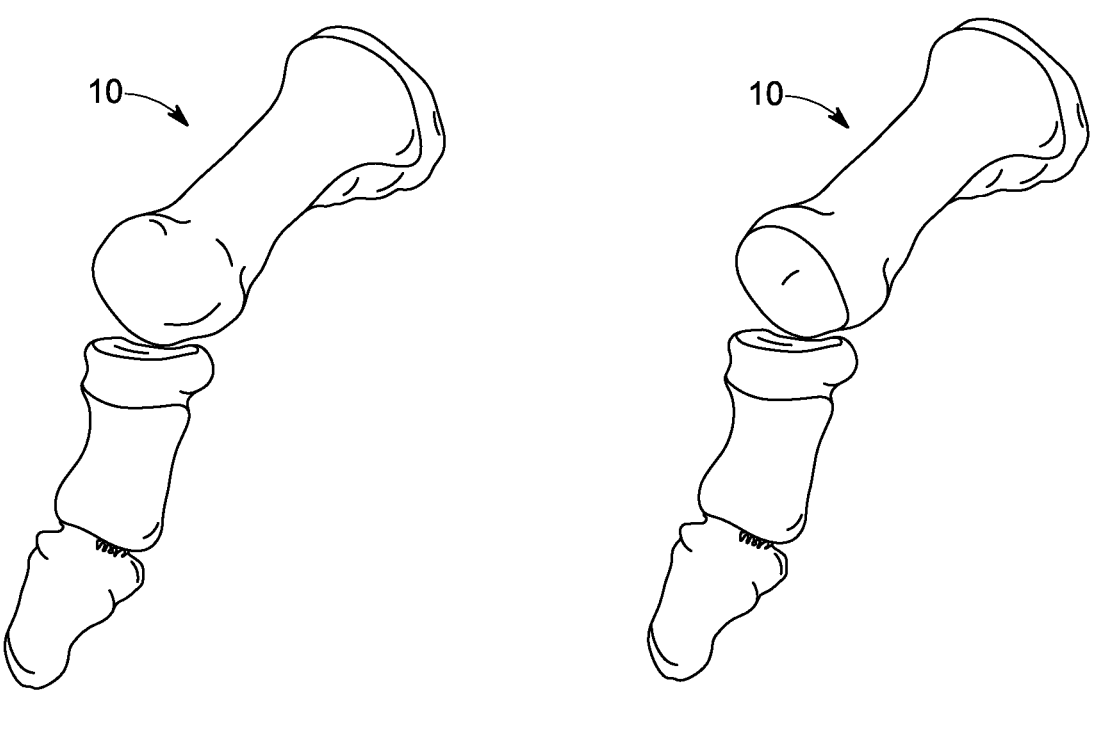
FIG. 25          FIG. 26
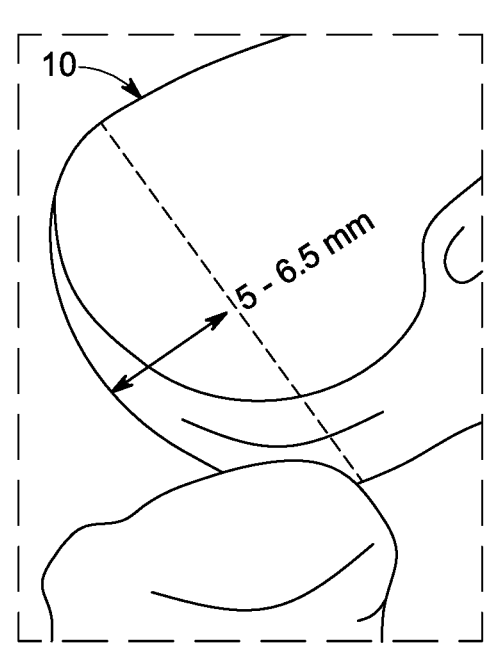
FIG. 27

500

450

100

| Size | Head Diameter (mm) | Stem Length (mm) | Stem Diameter (mm) | Head Thickness (mm) | Redius of Curvature (mm) |
|------|--------------------|-------------------|---------------------|---------------------|--------------------------|
| 14mm | 14 | 8.5 | 6.5 | 4.0 | 9.9 |
| 16mm | 16 | 10.0 | 6.5 | 4.0 | 12.7 |
| 18mm | 18 | 11.0 | 6.5 | 5.0 | 12.5 |
| 20mm | 20 | 12.0 | 7.5 | 5.0 | 14.7 |
| 22mm | 22 | 13.0 | 7.5 | 5.0 | 17.5 |

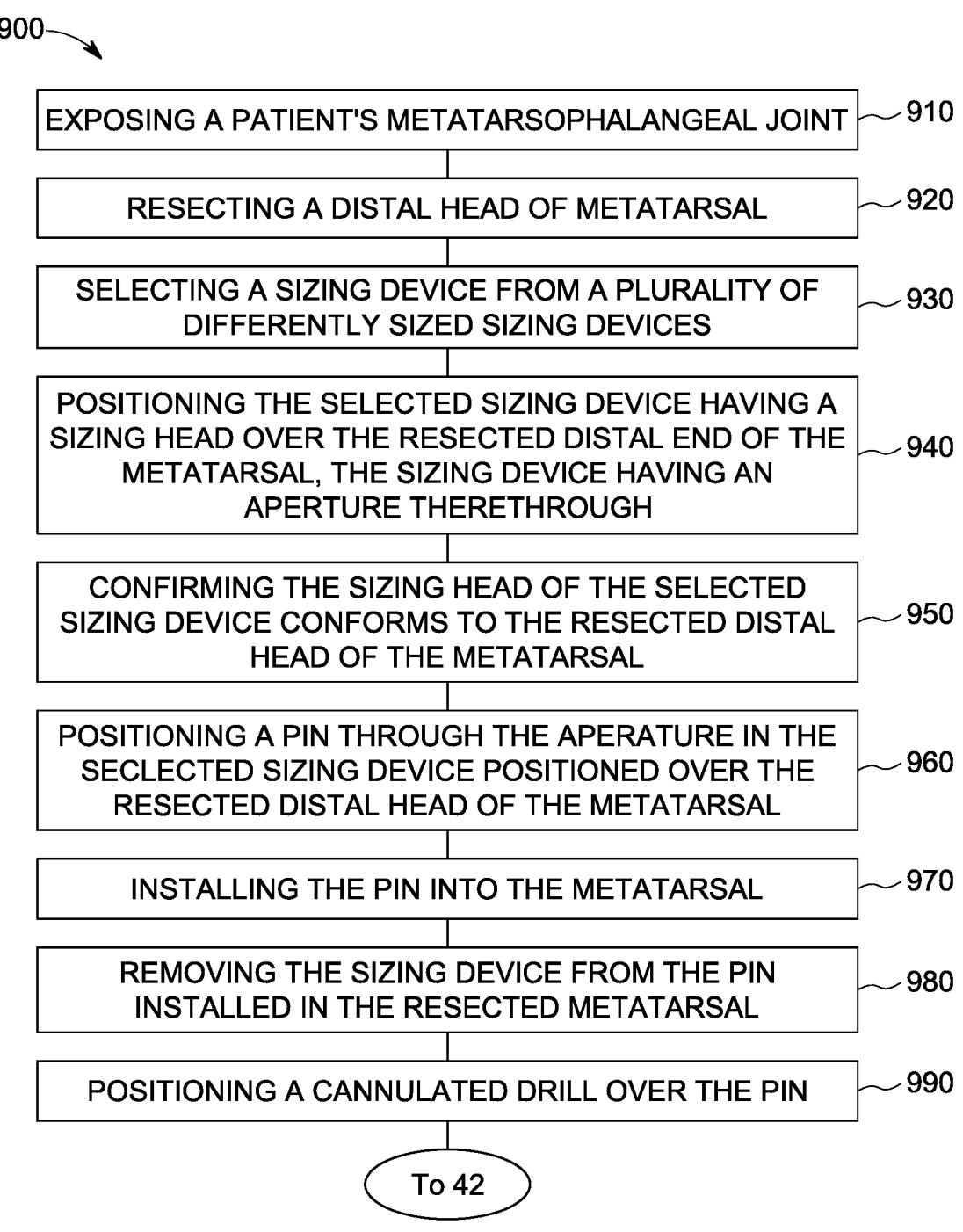

900

EXPOSING A PATIENT'S METATARSOPHALANGEAL JOINT — 910

RESECTING A DISTAL HEAD OF METATARSAL — 920

SELECTING A SIZING DEVICE FROM A PLURALITY OF DIFFERENTLY SIZED SIZING DEVICES — 930

POSITIONING THE SELECTED SIZING DEVICE HAVING A SIZING HEAD OVER THE RESECTED DISTAL END OF THE METATARSAL, THE SIZING DEVICE HAVING AN APERTURE THERETHROUGH — 940

CONFIRMING THE SIZING HEAD OF THE SELECTED SIZING DEVICE CONFORMS TO THE RESECTED DISTAL HEAD OF THE METATARSAL — 950

POSITIONING A PIN THROUGH THE APERATURE IN THE SECLECTED SIZING DEVICE POSITIONED OVER THE RESECTED DISTAL HEAD OF THE METATARSAL — 960

INSTALLING THE PIN INTO THE METATARSAL — 970

REMOVING THE SIZING DEVICE FROM THE PIN INSTALLED IN THE RESECTED METATARSAL — 980

POSITIONING A CANNULATED DRILL OVER THE PIN — 990

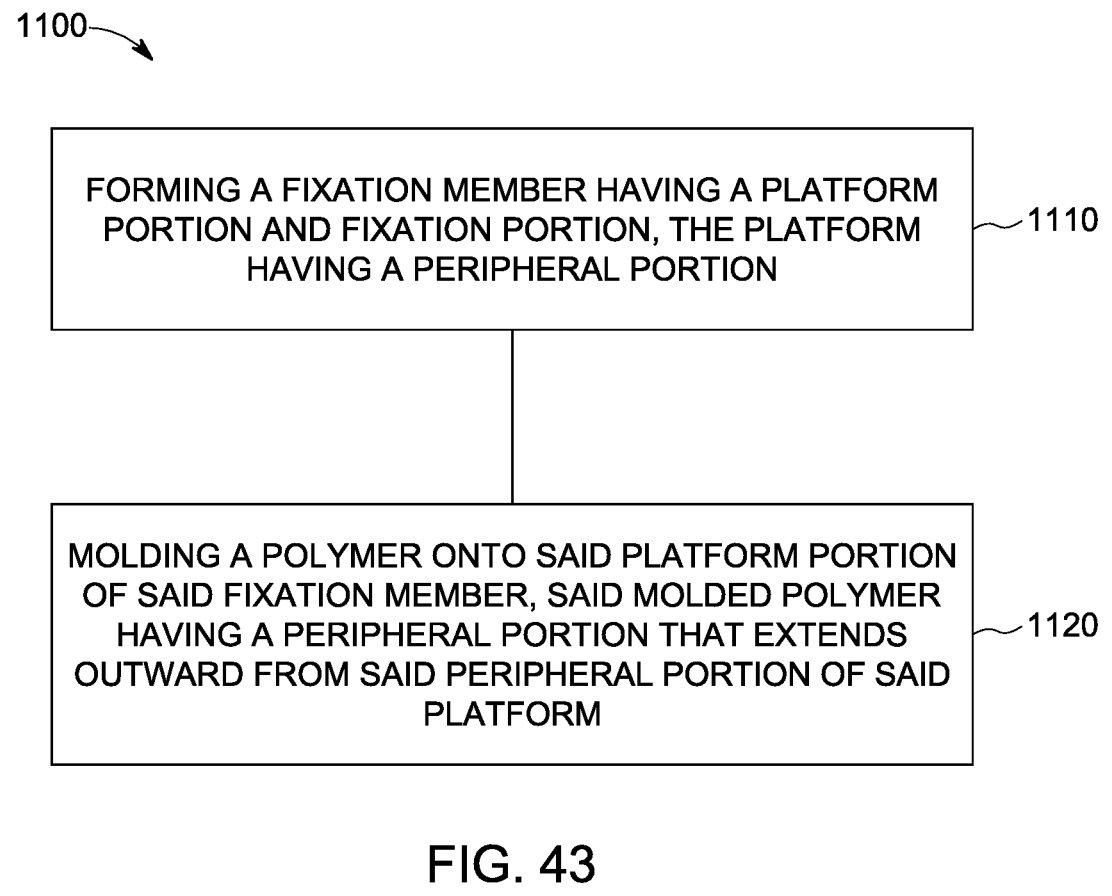

FORMING A FIXATION MEMBER HAVING A PLATFORM PORTION AND FIXATION PORTION, THE PLATFORM HAVING A PERIPHERAL PORTION — 1110

MOLDING A POLYMER ONTO SAID PLATFORM PORTION OF SAID FIXATION MEMBER, SAID MOLDED POLYMER HAVING A PERIPHERAL PORTION THAT EXTENDS OUTWARD FROM SAID PERIPHERAL PORTION OF SAID PLATFORM — 1120

FIG. 43

TOE IMPLANT ASSEMBLIES, KITS, SURGICAL METHODS, AND METHODS OF MANUFACTURING

CROSS REFERENCE TO RELATED APPLICATION

This application is a by-pass continuation of PCT International Application No. PCT/US2022/019334, filed Mar. 8, 2022, and entitled "Toe Implant Assemblies, Kits, Surgical Methods, and Methods of Manufacturing" which claims priority benefit under 35 U.S.C. § 119(e) of U.S. Provisional Application No. 63/158,405 filed Mar. 9, 2021 and entitled "Toe Implant Assemblies, Kits, Surgical Methods, and Methods of Manufacturing", which are incorporated herein by reference in their entirety.

TECHNICAL FIELD

The present disclosure relates generally to surgical implants for use in repairing a joint. More particularly, but not exclusively, the present disclosure relates to surgical implant assemblies for replacing a portion of a human toe joint and related kits, surgical methods, and methods of manufacturing.

BACKGROUND OF THE INVENTION

The first metatarsophalangeal (MTP) joint is a complex joint of the foot where bones, tendons, and ligaments work together to transmit and distribute the body's weight, especially during movement. Cartilage may act as a pad and/or spacer between the first metatarsal and the proximal phalanx to reduce friction between the bones and prevent the bones from articulating against each other.

Active persons may put continuous stress on the MTP joint over time, which may eventually wear out the articular cartilage of the MTP joint and lead to the onset of arthritis. This condition, known as hallux rigidus, causes loss of movement and pain in the MTP joint. The MTP joint may also be damaged due to injury or genetic defects, which may cause deterioration and/or loss of the articular cartilage, thereby limiting a person's range of motion. In many situations, non-operative treatments may provide relief, but individuals with advanced stages of MTP cartilage damage may need surgery.

Current surgical treatments for cartilage defects may include microfracture surgery, microdrilling techniques, osteoarticular transfer system (OATS) cartilage repair surgery, autologous chondrocyte implantation (ACI) or matrix-induced ACI (mACI), cheilectomy, MTP arthrodesis, MTP joint replacement (e.g., total, or partial joint arthroplasty), fusion, and/or other techniques. However, some patients may not be good candidates for certain surgical techniques for various reasons (e.g., a patient's bone quality, desired mobility, etc.). Additionally, existing implants used for treating damaged articular cartilage at the MTP joint may cause various unwanted side-effects including, but not limited to, failure due to shearing stress, loosening of the implant device, subsidence, fragmentation, fractures, breakage, misalignment, recurrence of deformity, limited joint motion, development of plantar keratosis, development of tenderness around the joint, development of long flexor tendonitis, development of metatarsalgia, and development of metallosis.

SUMMARY OF THE INVENTION

Shortcomings of the prior art are overcome and additional advantages are provided through the provision, in one embodiment, of a surgical method, which includes for example, exposing a patient's metatarsophalangeal joint, resecting a distal head of metatarsal, selecting a sizing device from a plurality of differently sized sizing devices, positioning the selected sizing device having a sizing head over the resected distal end of the metatarsal, the sizing device having an aperture therethrough, confirming the sizing head of the selected sizing device conforms to the resected distal head of the metatarsal, positioning a pin through the aperture in the selected sizing device positioned over the resected distal head of the metatarsal, installing the pin into the metatarsal, removing the selected sizing device from the pin installed in the resected metatarsal, positioning a cannulated drill over the pin, forming, with the cannulated drill over the pin, a cavity around the pin in the resected metatarsal, removing the cannulated drill from the cavity and from the pin installed in the resected metatarsal, removing the pin from the resected metatarsal and from the cavity in the resected metatarsal, selecting a trialing device from a plurality of differently sized trialing devices based on the sizing head of the sizing device, positioning a fixation member of the selected trialing device in the cavity in the resected metatarsal and a bearing member of the trialing device over the resected metatarsal, removing the selected trialing device from the resected metatarsal, selecting a toe implant assembly from a plurality of differently sized toe implant assemblies based on the sizing head of the selected sizing device and/or the size of the bearing member of the selected trialing device, and installing a fixation member of the selected toe implant assembly in the cavity with a tamping device in the resected metatarsal so that a bearing member of the toe implant assembly is disposed over the resected metatarsal.

In another embodiment, a toe implant assembly includes for example, a bearing member having a curved interface surface having a peripheral portion, and a fixation member having a platform portion and fixation portion, the platform portion having a peripheral portion sized smaller than the peripheral portion of the bearing member. The fixation member is coupled to the bearing member so that the peripheral portion of the bearing member extends outwardly from the peripheral portion of the platform portion.

In another embodiment, a kit includes, for example, a plurality of differently sized sizing devices, at least one cannulated drill, a tamping device, and a plurality of correspondingly sized trialing devices having a bearing member and fixation member, the bearing member having a curved interface surface having a first diameter, and the fixation member coupled to the bearing member, the fixation member having a diameter less than or equal to the first diameter.

In another embodiment, a method of manufacturing a toe implant includes, for example, forming a fixation member having a platform portion and fixation portion, the platform having a peripheral portion, and molding a polymer onto the platform portion of the fixation member, the molded polymer having a peripheral portion that extends outward from the peripheral portion of the platform.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 11 is a side elevational view of a toe implant assembly, according to an embodiment of the present disclosure;

FIG. 12 is an exploded, side elevational view of the toe implant assembly of FIG. 11, according to an embodiment of the present disclosure;

FIG. 13 is an exploded, bottom perspective view of the toe implant assembly of FIG. 11, according to an embodiment of the present disclosure;

FIG. 18 is a front perspective view of a sizing device, according to an embodiment of the present disclosure;

FIG. 19 is a rear perspective view of the sizing device of FIG. 18, according to an embodiment of the present disclosure;

FIG. 20 is a front perspective view of a cannulated drill bit or reamer, according to an embodiment of the present disclosure;

FIG. 21 is a rear perspective view of the cannulated drill bit or reamer of FIG. 20, according to an embodiment of the present disclosure;

FIGS. 25-39 illustrate a surgical method for replacing a portion of a human toe joint, according to an embodiment of the present disclosure;

FIG. 40 is a table of exterior toe implant assembly dimensions for a plurality of toe implant assemblies, according to an embodiment of the present disclosure;

FIGS. 41 and 42 are flowcharts illustrating a surgical method for replacing a portion of a human toe joint, according to an embodiment of the present disclosure;

FIG. 43 illustrates a flowchart of a method for manufacturing a toe implant assembly, according to an embodiment of the present disclosure;

DETAILED DESCRIPTION OF THE INVENTION

Figures 1, 2:
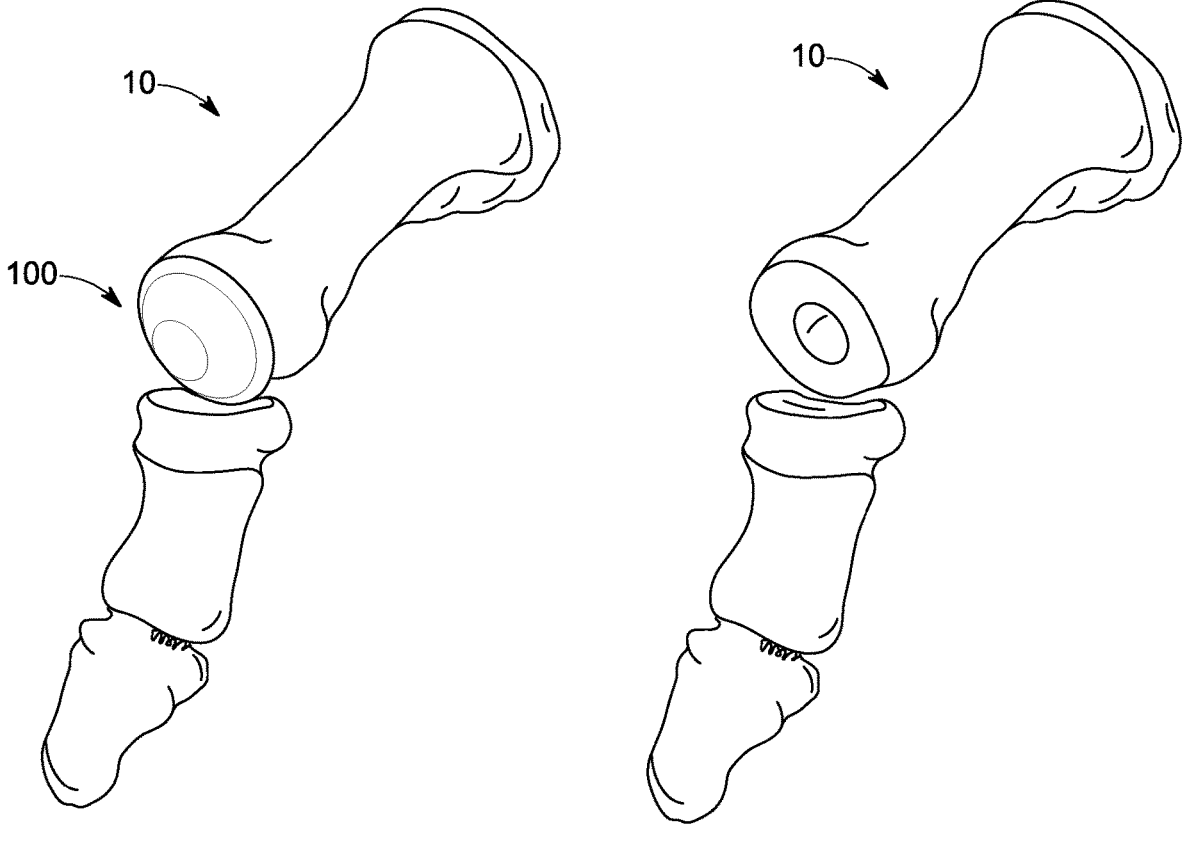
FIG. 1 is a perspective view of a toe implant assembly secured to a resected metatarsal bone, according to an embodiment of the present disclosure.
FIG. 2 is a perspective view of the resected metatarsal bone of FIG. 1 with the toe implant assembly removed illustrating a cavity in the resected metatarsal bone, according to an embodiment of the present disclosure.
Figure 3:
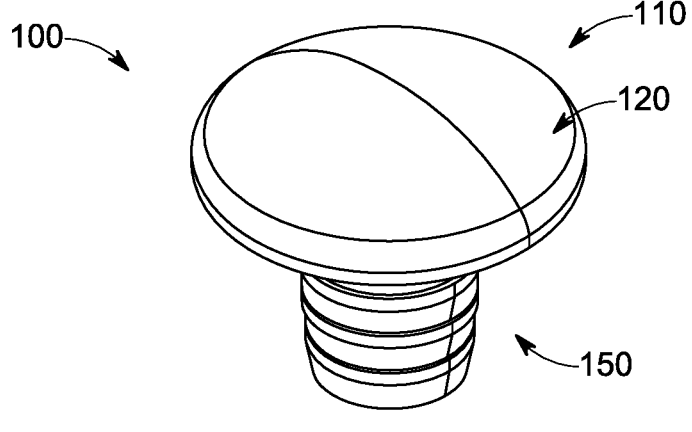
FIG. 3 is a top perspective view of the toe implant assembly of FIG. 1, according to an embodiment of the present disclosure.
Figure 4:
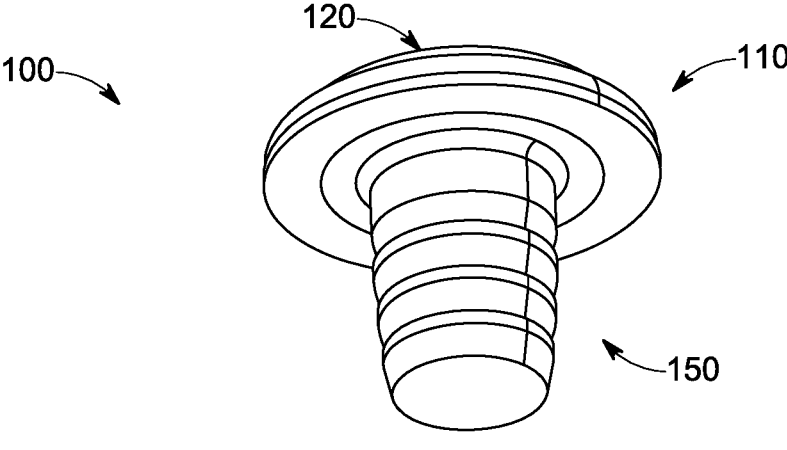
FIG. 4 is a bottom perspective view of the toe implant assembly of FIG. 3, according to an embodiment of the present disclosure.

Generally stated, disclosed herein are toe implant assemblies for replacement of a portion of a human toe joint, as well as related kits, surgical methods, and methods of manufacturing or fabrication.

The present disclosure may provide improved toe implant assemblies for use in treating articular cartilage damage of the MTP joint. For example, the toe implant assemblies may enable a patient to maintain motion of the MTP joint and may provide relief from symptoms associated with articular cartilage damage and/or disease without unwanted side-effects.

In this detailed description and the following claims, the words proximal, distal, anterior or plantar, posterior or dorsal, medial, lateral, superior and inferior are defined by their standard usage for indicating a particular part or portion of a patient's body, a bone, a device, or an implant according to the relative disposition of the patient or directional terms of reference. For example, "proximal" means a particular part or portion of a patient's extremity, a bone, a device, or implant nearest the torso, while "distal" indicates the portion of the patient's extremity, bone, device, or implant farthest from the torso. As for directional terms, "anterior" is a direction towards the front side of the body, bone, device, or implant, "posterior" means a direction towards the back side of the body, bone, device, or implant, "medial" means towards the midline of the body, "lateral" is a direction towards the sides or away from the midline of the body, "superior" means a direction above and "inferior" means a direction below another object or structure. Further, specifically in regard to the foot, the term "dorsal" refers to the top of the foot and the term "plantar" refers the bottom of the foot.

Similarly, positions or directions may be used herein with reference to anatomical structures or surfaces. For example, as the current devices, instrumentation and methods are described herein with reference to use with the bones of the foot, the bones of the foot may be used to describe the surfaces, positions, directions or orientations of the toe implant, kits for implant installation, and surgical methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the device and surgical methods, and the aspects, components, features and the like thereof, described and/or illustrated herein may be changed, varied, modified, reconfigured, or otherwise altered for use or association with another side of the body for a same or similar purpose without departing from the spirit and scope of the present disclosure. For example, the devices, instrumentation and methods, and the aspects, components, features and the like thereof, described herein with respect to a left toe may be mirrored so that they likewise function with a right toe and vice versa. Further, the devices, systems, instrumentation and methods, and the aspects, components, features and the like thereof, disclosed herein are described with respect to a toe for brevity purposes, but it should be understood that the devices, systems, instrumentation, and methods may be used with other bones of the body having similar structures.

The present disclosure provides a solution to medical professionals for the treatment of patients with damaged articular cartilage in the metatarsophalangeal (MTP) joint. In particular, disclosed herein are toe implant assemblies intended to replicate normal anatomy of a patient's metatarsal distal head (or in other embodiments, a phalangeal proximal head) by recreating the original articular surface geometry. The articulating portion of the metatarsal distal head implant is intended to be generally convex (whereas the articulating portion of the phalangeal distal head implant is intended to be generally concave). Further, the toe implant assemblies described herein may serve as a replacement pad and/or spacer by recreating the MTP joint space and replicating function of the articular cartilage.

Referring to the drawings, wherein like reference numerals are used to indicate like or analogous components throughout the several views, and with reference to FIGS. 1 and 2, there is illustrated an exemplary embodiment of a biocompatible toe implant assembly 100 (FIG. 1) secured to a resected metatarsal bone 10, according to an embodiment of the present disclosure. Toe implant assembly 100 may be operable to restore the normal anatomy of a patient's metatarsal distal head (or in other embodiments, phalangeal proximal head) by recreating the original articular surface geometry.

Figure 5:
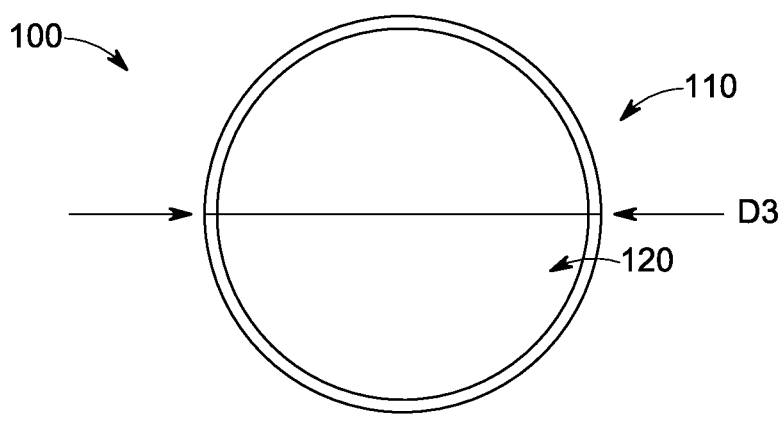
FIG. 5 is a top view of the toe implant assembly of FIG. 3, according to an embodiment of the present disclosure.
Figure 6:
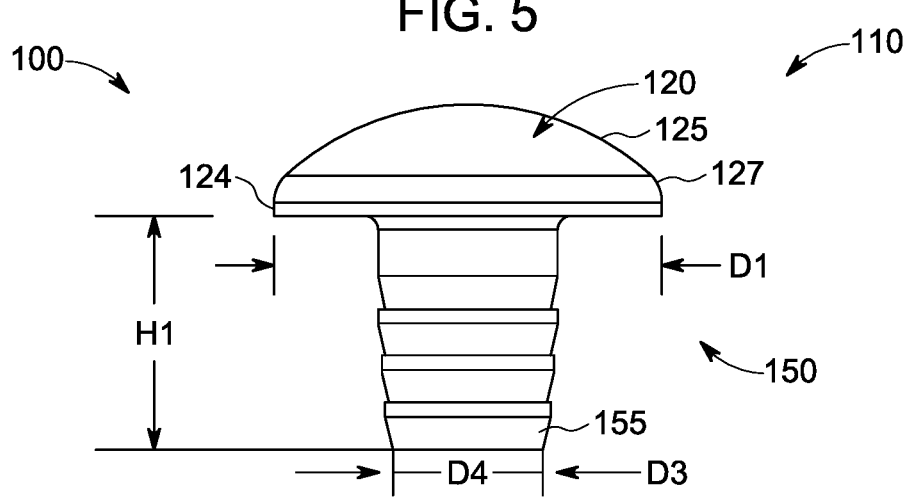
FIG. 6 is a side elevational view of the toe implant assembly of FIG. 3, according to an embodiment of the present disclosure.
Figure 7:
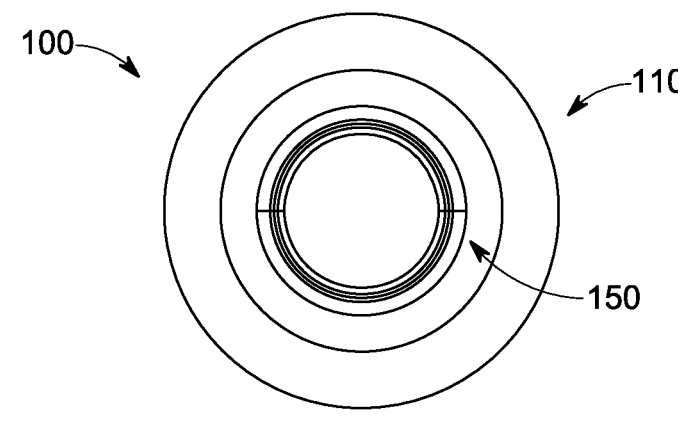
FIG. 7 is a bottom view of the toe implant assembly of FIG. 3, according to an embodiment of the present disclosure.
Figure 8:
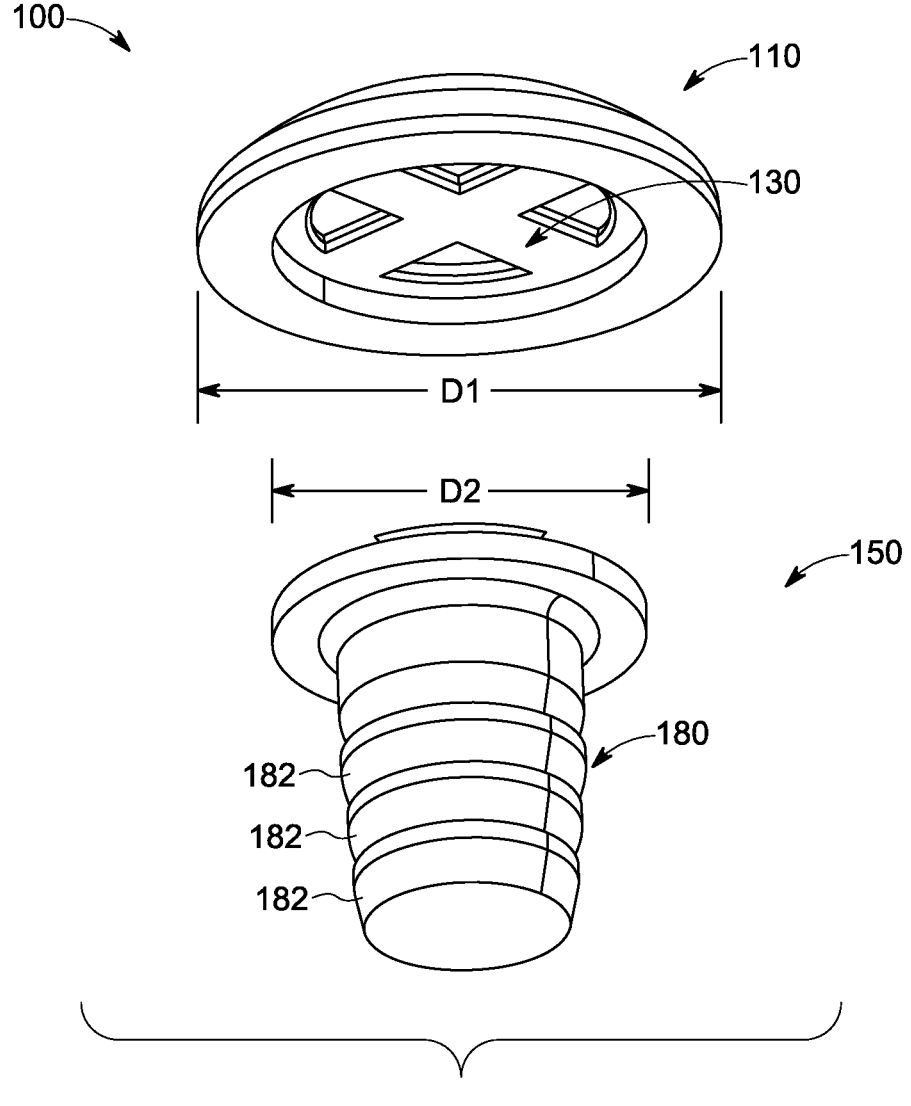
FIG. 8 is an enlarged, exploded bottom perspective view of the toe implant assembly of FIG. 3, according to an embodiment of the present disclosure.
Figure 9:
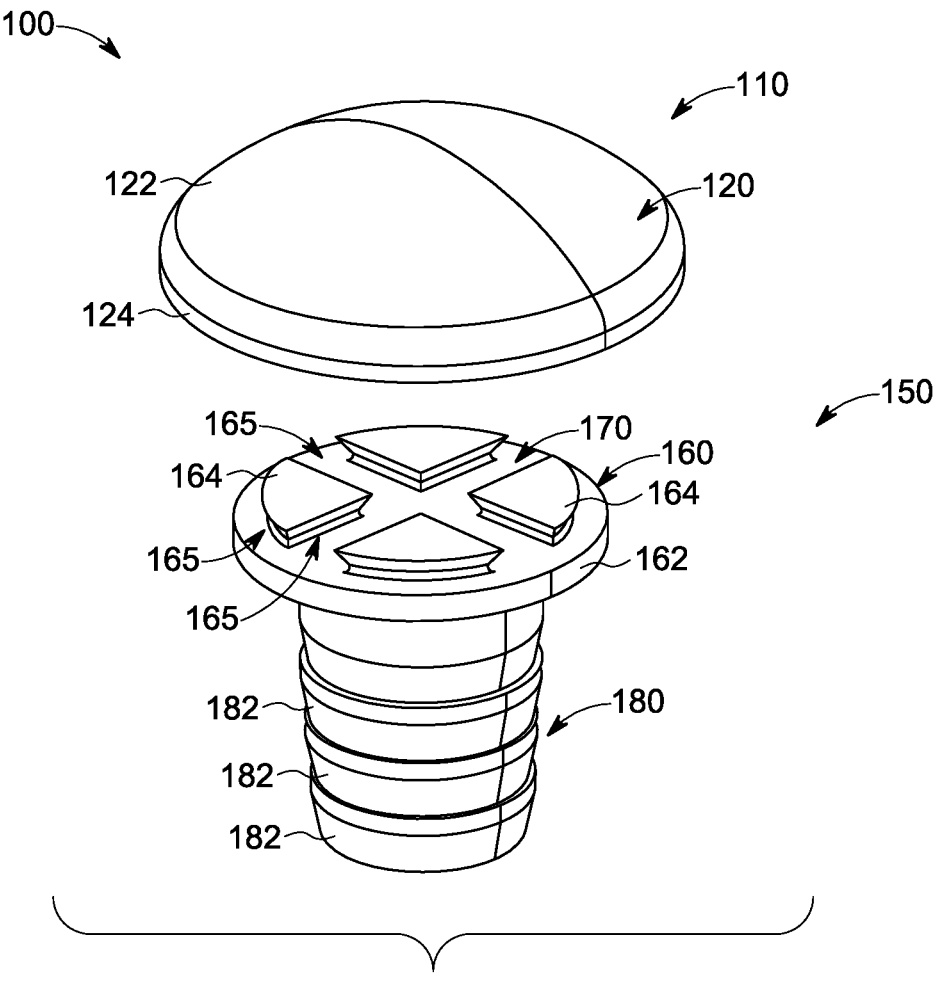
FIG. 9 is an enlarged, exploded top perspective view of the toe implant assembly of FIG. 3, according to an embodiment of the present disclosure.

With reference to FIGS. 3-7, the toe implant assembly 100 may include a bearing member 110 and a fixation member 150, according to an embodiment of the present disclosure. The toe implant assembly 100 may include fixation member 150 attached or coupled to the bearing member 110. In this illustrated embodiment, the bearing member 110 may include an articulating member or curved interface surface 120. The fixation member 150 may include a cylindrical platform portion 160 (FIGS. 8 and 9) and a fixation portion 180. In this illustrated embodiment, the fixation portion 180 may include a plurality of tapered cylindrical sections 182 (FIGS. 8 and 9). In addition, the tapered cylindrical sections may progressively get smaller toward the distal end, i.e., the outer portions of the cylindrical sections may get progressively smaller so that the fixation member may taper from the bottom of the bearing member to the distal end of the fixation portion 180 as best shown in FIG. 5.

As shown in FIG. 8, the bearing member 110 may have a coupling portion 130. As shown in FIG. 9, the fixation member 150 may include a coupling portion 170. As described in greater detail below, the coupling portion 130 (FIG. 8) of the bearing member 110 is connectable to the coupling portion 170 (FIG. 9) of the fixation member 150.

With reference still to FIG. 9, the curved interface surface 120 of the bearing member 110 of the toe implant assembly 100 may be designed to replicate the normal anatomy of a patient's metatarsal head. The curved interface surface 120 may include a non-constant curved surface 122, for example, or may be a constant radial surface similar to an outer portion of a sphere. The curved interface surface 120 of the bearing member 110 may be, for example, generally convex. Additionally, the bearing member 110 may include, for example, a second surface 124 that is generally cylindrical and may be commensurate or larger in diameter than the cylindrical platform portion 160 of the fixation member 150. As shown in FIG. 5, the curved interface surface 120 may include, for example, an upper curved edge 125 and a lower curved edge 127, where the upper curved edge 125 is a relatively gradual curve, and the lower curved edge 127 is a relatively steep curve. Further, the lower curved edge 127 may be joined to the upper curved edge 125 and commensurate in diameter with the second surface 124. The articulating or bearing member 110 may have a diameter D1 in the range between about 14 mm to about 22 mm.

The articulating member or bearing member 110 may include a hydrophilic polymer, which may, for example, include hyaluronic acid and ultrahigh molecular weight polyethylene (UHMWPE). Other embodiments may include, for example, polyurethane, polyether ether ketone (PEEK), or a hydrogel. Further examples of suitable polymeric materials are described in U.S. Pat. No. 7,662,954, issued to James, et al. entitled "Outer Layer Having Entanglement Of Hydrophobic Polymer Host And Hydrophilic Polymer Guest," which is incorporated herein by reference in its entirety. Advantageously, polymer combinations such as hyaluronic acid with UHMWPE may, for example, attract lubricating joint fluid to the bearing member, enabling the bearing member to include self-lubricating properties.

With reference again to FIG. 9, the fixation member 150 may include at least one standard metallic biocompatible implant material such as, for example, titanium, cobalt chrome, or other acceptable stainless steels.

The cylindrical platform portion 160 of the fixation member 150 may include a constant thickness disc-shaped member 162 and raised portions 164 defining dovetail channels 165 capable of receiving the polymer during a manufacturing process. The articulating member or bearing member 110 may be attached to the fixation member 150 via a locking mechanism which for example purposes is configured as an undercut dovetail locking arrangement. The angle of the vertical walls of the dovetail locking arrangement are generally less than 90 degrees, which provides resistance against the articulating member or bearing member 110 from dislodging from the fixation member 150. The nature of the dovetail feature may also prevent the articulating member or bearing member 110 from rotating relative to the cylindrical platform portion 160 of the fixation member 150. As will be appreciated, portions of the dovetail cuts may be disposed perpendicular to each other, resulting in a cross-shaped arrangement. Having multiple directional cuts helps to ensure that there is no translational or sliding movement of the articulating member or bearing member 110 relative to the cylindrical platform portion 160 of the fixation member 150. Alternative modes of fixing the articulating member or bearing member 110 to the cylindrical platform portion 160 of the fixation member 150 may also include a snap-fit mechanism, an adhesive material, or an alternative locking channel. A dovetail locking mechanism for use in the present disclosure is further described in U.S. Pat. No. 9,216,085 issued to Schwartz et al. and U.S. Pat. No. 9,526,619 issued to Schwartz et al., which patents are incorporated herein by reference in their entirety.

With reference again to FIG. 8, a peripheral diameter D1 of the bearing member 110 may be larger than the peripheral diameter D2 of the cylindrical platform 160 so that bearing member 110 extends over and fits onto the cylindrical platform 160.

In one embodiment, the plurality of tapered cylindrical sections 182 of the fixation member 150 may include titanium-based porous material, which may also include at least one void capable of receiving bone ingrowth after implantation. Additionally, the fixation components may have a non-circular shape for at least a portion of the component. For instance, the fixation component may have a cross section of a polygon at least such as a triangle, square, rectangle, pentagon, hexagon, septagon, octagon. The non-circular cross section could facilitate anti-rotation characteristics in the bone.

With reference again to FIG. 5, the fixation member 150 may include a distal tapered cylindrical portion 155 having an angular surface capable of providing a clearance fit at the onset of implantation. For instance, the angular surface may be angled such that the tapered cylindrical portion 155 includes, for example, a first diameter D3 at the top of the tapered cylindrical portion 155, and a second diameter D4 at the bottom of the tapered cylindrical portion 155. Further, the second diameter D4 may be less than or equal to the first diameter D3. The angular surface may include, for example, any angle capable of providing a clearance fit at the onset of implantation. In particular, the angular surface may be inserted into a patient's resected metatarsal bone such that the diameter at the bottom of the tapered cylindrical portion 155 does not engage with bone. For instance, according to one embodiment, the angular surface may be angled, for example, approximately 20 degrees inward from the first diameter D3 to the second diameter D4. In other embodiments, the angular surface may include an angle that is, for example, larger or smaller. The fixation member 150 may include a total length H1 in the range between about 8.5 mm and about 13 mm and include a diameter that is within the diameter of the articulating or bearing member being in the range between 6.5 mm to about 7.5 mm.

Figure 10:
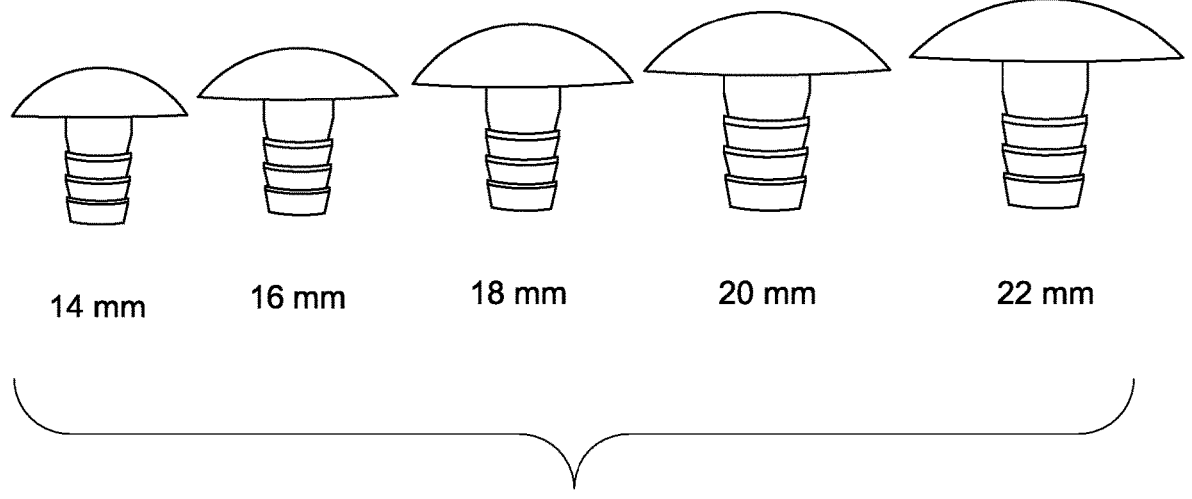
FIG. 10 are side elevational views of a plurality of different sized toe implant assemblies similar to the toe implant assembly of FIG. 3, according to an embodiment of the present disclosure.

With reference to FIG. 10, the toe implant assembly 100 may be designed in multiple sizes to allow selection by a medical professional based on the width and/or length of the particular metatarsal bone being treated. According to some embodiments, the total diameter of the articulating member or bearing member 110 may be larger than the cylindrical platform portion. The diameter of the articulating member or bearing member may be within a range of about 14 mm to about 22 mm. The total diameter may be selected from a plurality of differently sizes based on the surface anatomy of a patient's resected metatarsal head. For example, sizes of the toe implant assemblies may include the diameter of the articulating or bearing member being, for example, 14 mm, 16 mm, 18 mm, 20 mm, and 22 mm. Additional sizes greater or less than the examples could be included as well. For instance, for smaller toes, example sizes could go as low as 9 mm to 13 mm in diameter or smaller.

FIGS. 11-14 illustrate a toe implant assembly 200 having an articulating member or bearing member 210 and a fixation member 250, according to an embodiment of the present disclosure. The toe implant assembly 200 may include fixation member 250 attached or coupled to the bearing member 210.

In this illustrated embodiment, the bearing member 210 may include a curved interface surface 220. The bearing member 210 may be essentially the same as bearing member 110 (FIGS. 3-10) described above. The fixation member 250 may include a cylindrical platform portion 260 and a fixation portion 280. The platform 260 of the fixation member 250 may be essentially the same as the platform 160 (FIG. 9) of the fixation member 150 (FIG. 9).

The fixation portion 280 may include a cylindrical support portion 240 and a porous sleeve 255. The cylindrical portion 240 may include a distal tapered cylindrical portion 256. The tapered cylindrical portion 256 may include an angular surface 257.

The tapered cylindrical portion 256 of the toe implant assembly 200 may also include the angular surface 257 capable of providing a clearance fit at the onset of implantation. For instance, the angular surface 257 may be angled such that the tapered cylindrical portion 256 includes, for example, a first diameter D5 at the top of the tapered cylindrical portion 256, and a second diameter D6 at the bottom of the tapered cylindrical portion 256. The second diameter may be less than or equal to the first diameter. The angular surface 257 may include, for example, any angle capable of providing a clearance fit at the onset of implantation. In particular, the angular surface 257 may be inserted into a patient's resected metatarsal bone such that the diameter at the bottom of the tapered cylindrical portion 256 does not engage with bone. For instance, according to one embodiment, the angular surface 257 may be angled, for example, approximately 20 degrees inward from the first diameter D5 to the second diameter D6. In other embodiments, the angular surface 257 may include an angle that is, for example, larger or smaller. The fixation member 250 may include a total length H2 in the range of between about 8.5 mm and about 13 mm.

Figure 14:
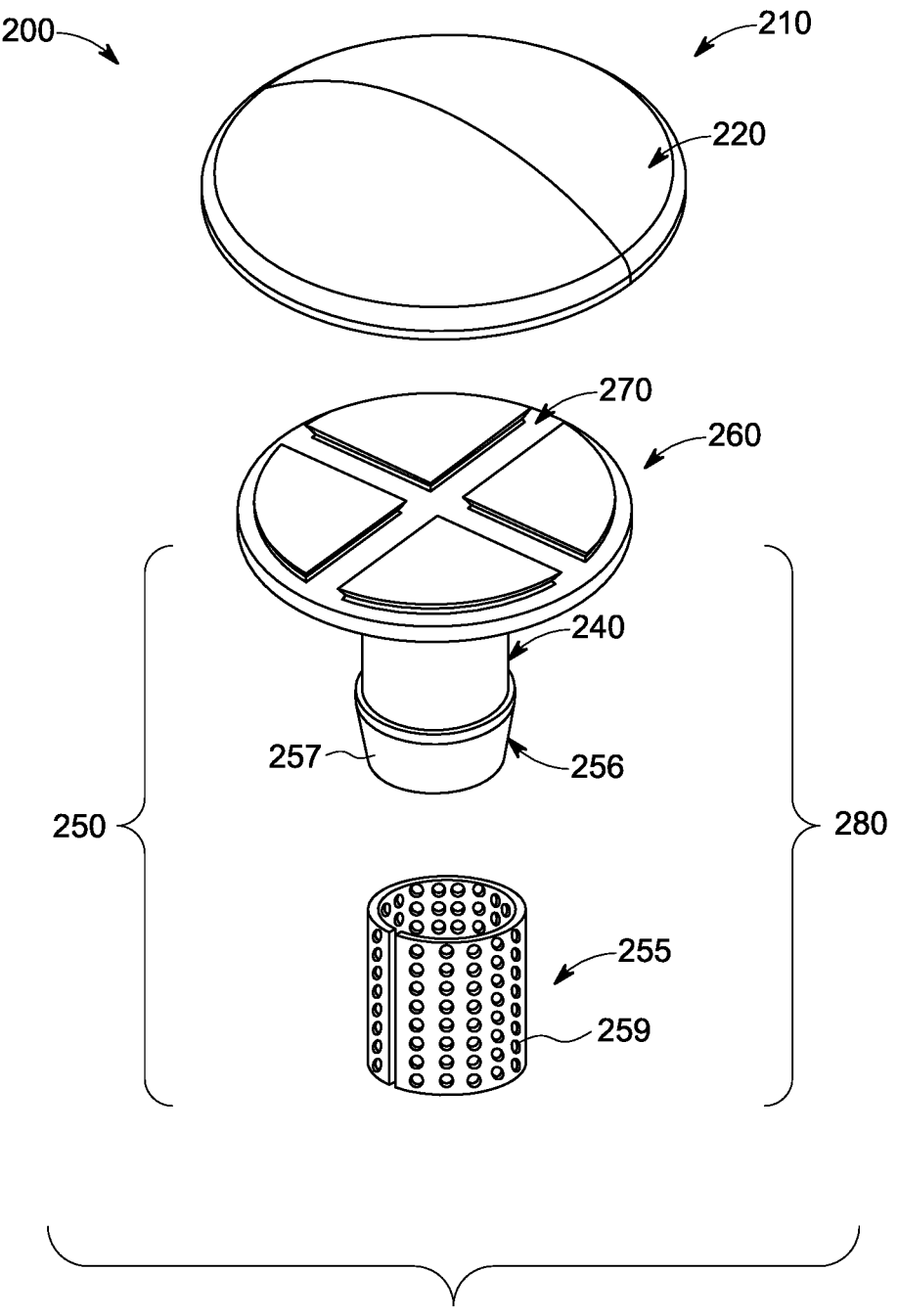
FIG. 14 is an exploded, top perspective view of the toe implant assembly of FIG. 11, according to an embodiment of the present disclosure.

With reference to FIGS. 13 and 14, the fixation member 250 may include the cylindrical support portion 240 having the tapered cylindrical portion 256. The sleeve 255 may be disposed on the cylindrical support portion 240. The sleeve 255 may be porous having a plurality of openings 259 extending therethrough.

Figure 15:
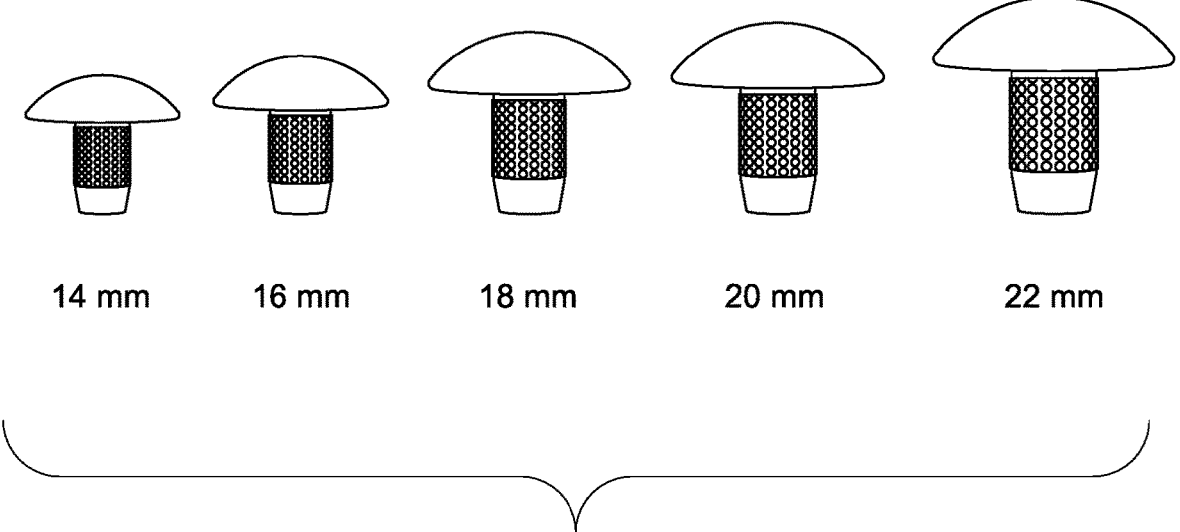
FIG. 15 are side elevational views of a plurality of different sized toe implant assemblies similar to the toe implant assembly of FIG. 11, according to an embodiment of the present disclosure.

With reference to FIG. 15, the toe implant assembly 200 may be designed in multiple sizes to allow the selection by a medical professional based on the width and/or length of the particular metatarsal bone being treated. According to some embodiments, the diameter of the articulating member or bearing member may be larger than the cylindrical platform portion. The total diameter of the articulating member or bearing member may be a diameter that is within a range of about 14 mm to about 22 mm. The total diameter may be selected from a plurality of different sizes based on the surface anatomy of a patient's resected metatarsal head.

For example, sizes of the toe implant assemblies may include, for example, 14 mm, 16 mm, 18 mm, 20 mm, and 22 mm. Additional sizes greater or less than the examples could be included as well. For instance, for smaller toes, example sizes could go as low as 9 mm to 13 mm in diameter or smaller.

Figure 16:
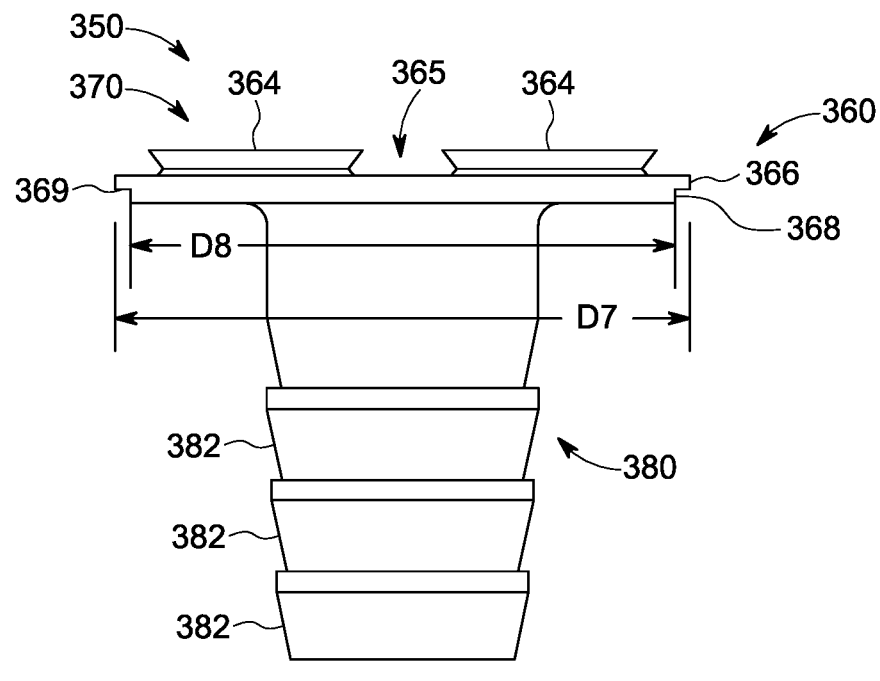
FIG. 16 is a side elevational view of a fixation member for a toe implant assembly, according to an embodiment of the present disclosure.

FIG. 16 illustrates a fixation member 350, according to an embodiment of the present disclosure. The fixation member 350 may include a cylindrical platform portion 360 and a fixation portion 380 having a plurality of tapered cylindrical sections 382. In this illustrated embodiment, the cylindrical platform portion 360 may include an additional coupling or locking feature for connecting to an articulating member or bearing member (not shown in FIG. 16).

The tapered cylindrical sections may progressively get smaller toward the distal end, i.e., the fixation member may taper. The plurality of tapered cylindrical sections 382 may be essentially the same as the plurality of tapered cylindrical sections 182 (FIG. 9) of the fixation member 150 (FIG. 9) described above.

The cylindrical platform portion 360 of the fixation member 350 may have a coupling portion 370 that may be essentially the same as the coupling portion 170 (FIG. 9) of fixation member 150 (FIG. 9), e.g., the raised portions 364 may define dovetail channels 365 capable of receiving the polymer forming an articulating member or bearing member (not shown in FIG. 16) during a manufacturing process.

In this illustrated embodiment, the cylindrical platform portion 360 may include a first upper platform portion 366 and a second lower platform portion 368, e.g., the platform may include two separate cylindrical platforms or portions having different peripheral portions or diameters. The purpose of the configuration of the cylindrical platform portion 360 is that it may allow an extra surface for the polymer articulating member or bearing member to be molded onto, thereby increasing the interface strength between the fixation portion and the bearing components. For example, the first upper platform portion 366 may have a diameter D7 that is greater than a diameter D8 of the second lower platform 368. In some embodiments, diameter D8 may be, for example, 0.03 inches less that diameter D7. In some embodiments, different portions 366 and 368 may have the same thickness, or in other embodiments may have different thicknesses. During the manufacturing process to form the polymer into the articulating member or bearing member (not shown in FIG. 16) on the cylindrical platform portion 360 of the fixation member 350, the articulating member or bearing member may be sized to extend around the perimeter of first upper platform 366 and under the bottom peripheral surface 369 of first upper platform portion 366 to further lock the articulating member or bearing member (not shown in FIG. 16) on the cylindrical platform portion 360 of the fixation member 350.

The articulating member or bearing member for use with fixation member 350 may be essentially the same as the articulating member or bearing member 170 (FIGS. 8 and 9) with the exception of extending around the periphery of first upper platform portion 366. Various toe implant assemblies may incorporate the features of the fixation member 350, e.g., the sizes of the toe implant assemblies may include the diameter of the articulating or bearing member being, for example, 14 mm, 16 mm, 18 mm, 20 mm, and 22 mm. Additional sizes greater or less than the examples could be included as well. For instance, for smaller toes, example sizes could go as low as 9 mm to 13 mm in diameter or smaller.

Figure 17:
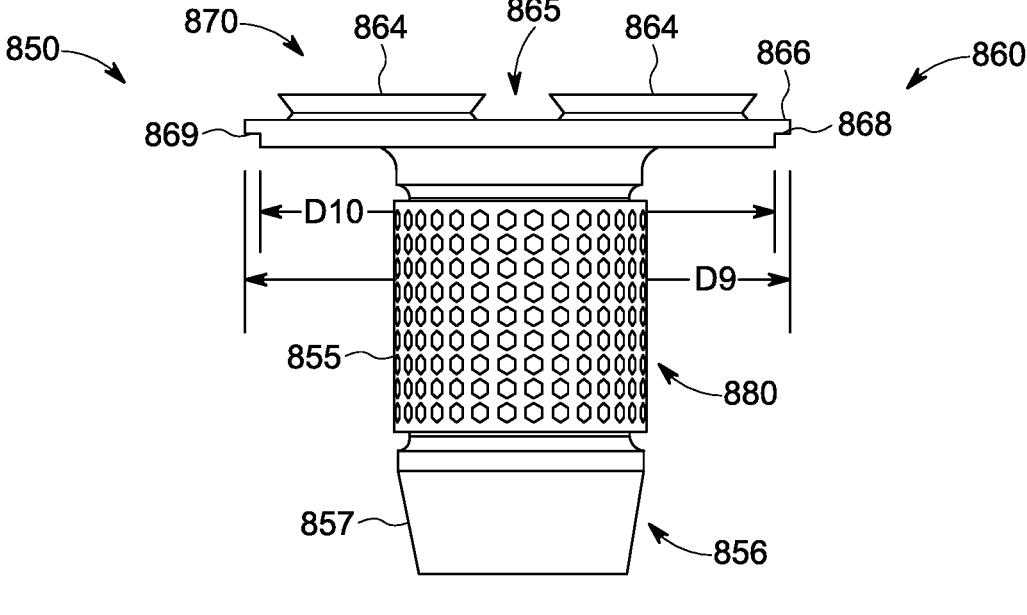
FIG. 17 is a side elevational view of a fixation member for a toe implant assembly, according to an embodiment of the present disclosure.

FIG. 17 illustrates a fixation member 850, according to an embodiment of the present disclosure. The fixation member 850 may include a cylindrical platform portion 860, a cylindrical portion 880 having a porous sleeve 855, and a tapered cylindrical portion 856. In this illustrated embodiment, the cylindrical platform portion 860 may include an additional coupling or locking feature for connecting to an articulating member or bearing member (not shown in FIG. 17).

As shown in FIG. 17, the cylindrical portion 880 having the porous sleeve 855 may be essentially the same as the cylindrical portion 254 (FIG. 12) having the porous sleeve 255 (FIG. 12) of the fixation member 250 (FIG. 12) described above.

The cylindrical platform portion 860 of the fixation member 850 as seen in FIG. 17, may have a coupling portion 870 that may be essentially the same as the coupling portion 270 (FIG. 14) of fixation member 250 (FIG. 14), e.g., the raised portions 864 may define dovetail channels 865 capable of receiving the polymer forming an articulating member or bearing member (not shown in FIG. 17) during a manufacturing process.

In this illustrated embodiment (see FIG. 17), the cylindrical platform portion 860 may include a first upper platform portion 866 and a second lower platform portion 868, e.g., the platform may include two separate cylindrical platforms or portions having different peripheral portions or peripheral diameters. The purpose of the configuration of the cylindrical platform portion 860 is that it may allow an extra surface for the polymer articulating member or bearing member to be molded onto, increasing the interface strength between the fixation and bearing components. For example, the first upper platform portion 866 may have a diameter D9 that is greater than a diameter D10 of the second lower platform 868. In some embodiments, diameter D10 may be, for example, 0.03 inches less than diameter D9. In some embodiments, different platform portions 866 and 868 may have the same thickness, or in other embodiments may have different thicknesses. During the manufacturing process to form the polymer into the articulating member or bearing member (not shown in FIG. 17) on the cylindrical platform portion 860 of the fixation member 850, the articulating member or bearing member may be sized to extend around the perimeter of first upper platform 866 and under the bottom peripheral surface 869 of the first upper platform portion 866 to further lock the articulating member or bearing member (not shown in FIG. 17) on the cylindrical platform portion 860 of the fixation member 850.

The articulating member or bearing member for use with fixation member 850 may be essentially the same as the articulating member or bearing member 270 (FIGS. 13 and 14) with the exception of extending around the periphery of first upper platform portion 866. Various toe implant assemblies may incorporate the features of the fixation member 850, e.g., the sizes of the toe implant assemblies may include the diameter of the articulating or bearing member being, for example, 14 mm, 16 mm, 18 mm, 20 mm, and 22 mm. Additional sizes greater or less than the examples could be included as well. For instance, for smaller toes, example sizes could go as low as 9 mm to 13 mm in diameter or smaller.

In the various embodiments, the diameter of platform portion of the fixation member may be less than the diameter of the bearing member. In the various embodiments, the diameter of platform portion of the fixation member may be equal to the diameter of the bearing member. In the various embodiments, the diameter of fixation portion of the fixation member may be less than the diameter of the bearing member. In the various embodiments, the diameter of fixation portion of the fixation member may be equal to the diameter of the bearing member. In the various embodiments, the distal end of the fixation portion of the member may tapered. In the various embodiments, the distal end of the fixation portion of the fixation member may have a constant or equal diameter.

The present disclosure may also be directed to a kit for use in repairing or replacing a portion of a human toe joint such as for use in treating articular cartilage damage in the MTP joint. As described below, a kit may include one or more sizing devices. The kit may also include one or more trial toe implants, and one or more toe implant assemblies such as those described above.

As shown in FIGS. 18 and 19, a sizing device 400 may be configured to engage the resected metatarsal surface. The sizing device 400 may include a generally planar body 140 having a sizing head 420 and an elongated handle 440. The sizing head 40 may include an engagement slot 425 through which a positioning device or pin may be inserted for aligning a cannulated drill or reamer. The sizing device 400 may be designed in multiple sizes to allow selection by a medical professional based on the width and/or length of the particular metatarsal bone being treated and used to determine a proper size for the toe implant assembly 100 (FIGS. 3-10), the toe implant assembly 200 (FIGS. 11-15), or the toe implant assemblies having a fixation member 350 and 850 (FIGS. 16 and 17) to be later inserted into the metatarsal head. A total diameter D6 of the sizing head 420 may be a diameter that is within a range, for example, of about 14 mm to about 22 mm. The total diameter may be selected from a plurality of different sizes based on the surface anatomy of a patient's resected metatarsal head. For example, a kit may include a plurality of sizing devices having different size sizing heads that may include, for example, 14 mm, 16 mm, 18 mm, 20 mm, and 22 mm sizing heads and which correspond to the size of the toe implant assemblies.

With reference to FIGS. 20 and 21, the kit may also include a cannulated drill bit or reamer 500 that includes at least one flute 510 or other cutting apparatus for drilling into the resected metatarsal head. Additionally, the cannulated drill bit or reamer 500 may include an engagement slot 520 through which a positioning device such as a pin may be inserted. The cannulated drill bit or reamer 500 and the at least one flute may be sized to correspond to an appropriate diameter of the implant fixation member of the toe implant assembly. The at least one flute 510 may be configured to resect or cut, during rotation of the drill bit, a portion of the resected metatarsal head. The drill bit or reamer 500 may also include a barrier or stop 530 to prevent the cannulated drill bit or reamer 500 from resecting too much bone from the resected metatarsal head. The drill bit or reamer 500 may include an engagement slot 520 configured to engage the positioning device or pin in order to provide proper alignment for the cannulated drill bit or reamer 500 relative to the metatarsal head.

Figure 22:
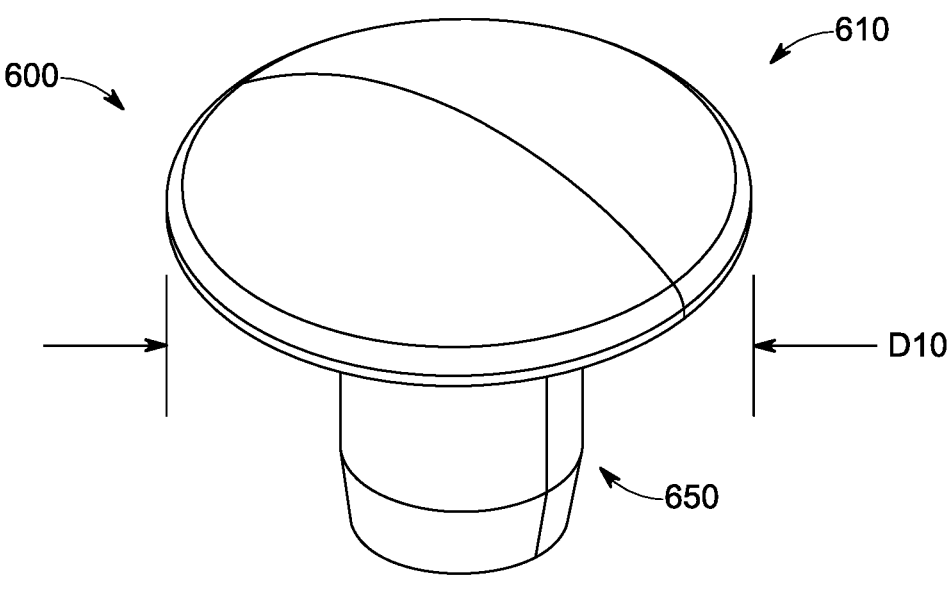
FIG. 22 is a top perspective view of a trialing device, according to an embodiment of the present disclosure.
Figure 23:
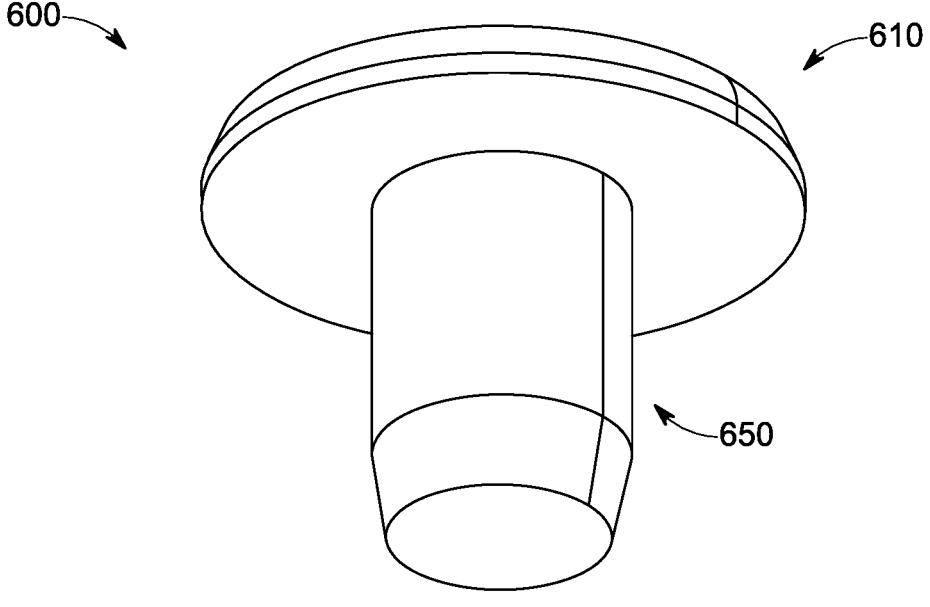
FIG. 23 is a bottom perspective view of the trialing device of FIG. 22, according to an embodiment of the present disclosure.

With reference to FIGS. 22 and 23, the kit may also include a trialing device 600 having a simulated bearing member 610 configured to engage and be positioned on the resected metatarsal surface and a simulated fixation member 650 configure to engage the cavity in the drilled metatarsal bone. The trialing device 600 may be sized to correspond to the corresponding bearing member and fixation member of the toe implant assembly. Additionally, the trialing device 600 may be designed to correspond to the diameter of the corresponding sizing device 400. The trialing device 600 may be designed in multiple sizes to allow for the selection by a medical professional based on the width and/or length of the particular metatarsal bone being treated. The total diameter D10 of the trialing device head may be a diameter that is within a range of about 14 mm to about 22 mm. The total diameter D10 may be selected from a plurality of different sizes based on surface anatomy of a patient's resected metatarsal head. For example, sizes may include 14 mm, 16 mm, 18 mm, 20 mm, and 22 mm.

Figure 24:
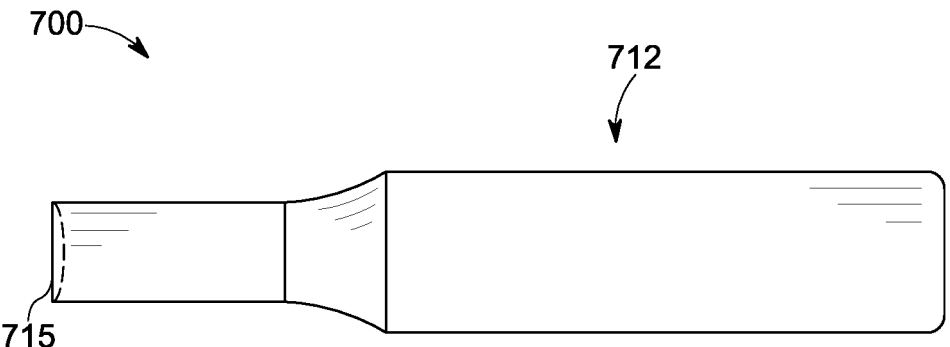
FIG. 24 is a side elevational view of a tamping device, according to an embodiment of the present disclosure.

As shown in FIG. 24, the kit may further include a tamping device 700 having an elongated body 712 with a concave surface 715 at one end. The concave surface 715 is configured to engage the bearing member of the toe implant assembly. The tamping device 700 may be sized to correspond to the curvature of the bearing member of the toe implant assembly.

A surgical method may include, for example, a process of exposing a patient's metatarsophalangeal joint. Additionally, the method may include resecting the metatarsal head and positioning a sizing device. Further, a positioning device or pin may be fixated into a patient's resected metatarsal head via the sizing device's engagement slot. The sizing device may be removed, and a cannulated drill bit may be positioned over the positioning device or pin via the cannulated drill bit's engagement slot. The method may also include drilling into the patient's resected metatarsal head to a predetermined depth. The cannulated drill bit and pin may be removed, and a trialing device may be placed into the resected metatarsal via the cavity created by the drill bit. The method may also include removing the trialing device and inserting the toe implant assembly into the patient's metatarsal. The toe implant assembly may be tamped into the patient's resected metatarsal head. The method may also include closing the patient's incision.

FIGS. 25-29 diagrammatically illustrate a surgical method for replacing a portion of a human toe joint, according to an embodiment of the present disclosure. Initially, with reference to FIG. 25, an assessment is made by making a small straight dorsal incision along the dorsal aspect of the first MTP joint to provide exposure of the capsule. Desirably, care may be taken to avoid nerve damage and to protect the EHL tendon. The joint is exposed such that access is perpendicular to the metatarsal head 10. Release of the lateral and medial soft tissues may be required.

As shown in FIG. 26, once the bone is exposed, the bone surface is prepared by resecting the distal head of the metatarsal bone by taking an appropriately sized sawblade and cutting the anterior surface until resection is complete. The width of the resected bone should be within about 5 mm to about 6.5 mm as shown in FIG. 27. This resection should bypass any tendon or critical soft tissue. The resection cut is made in an angled direction which aligns perpendicular with the normal axis. This creates a surface that aligns with the normal axis of the MTP joint.

Figure 28:
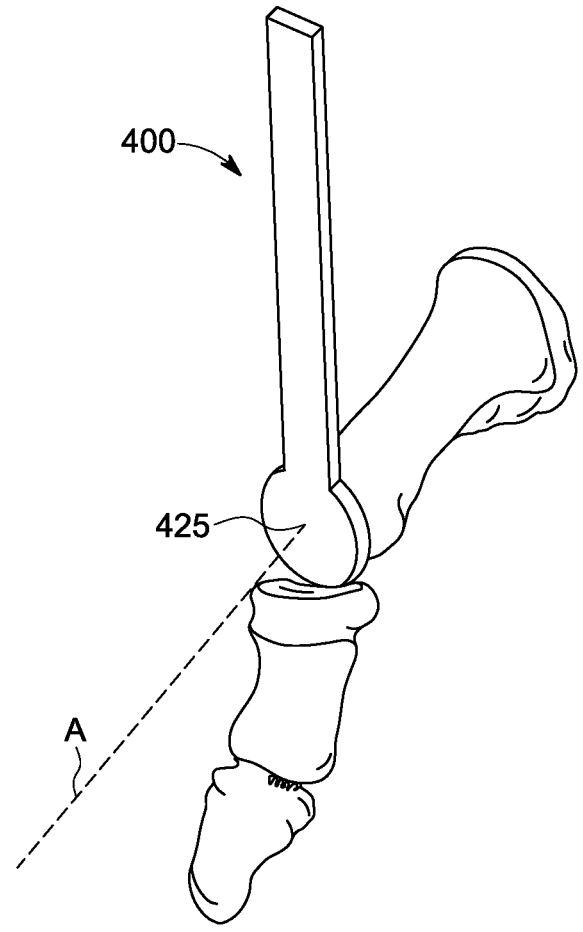
Figure 29:
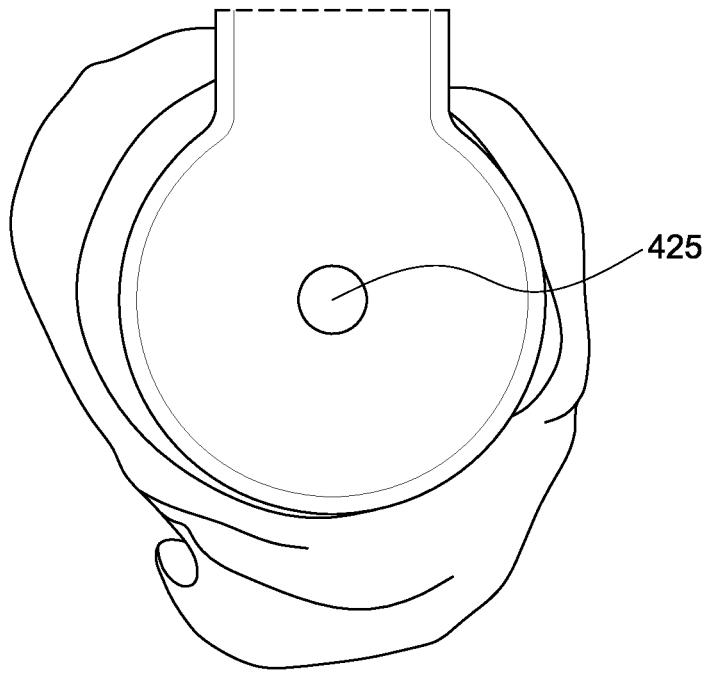
Figure 30:
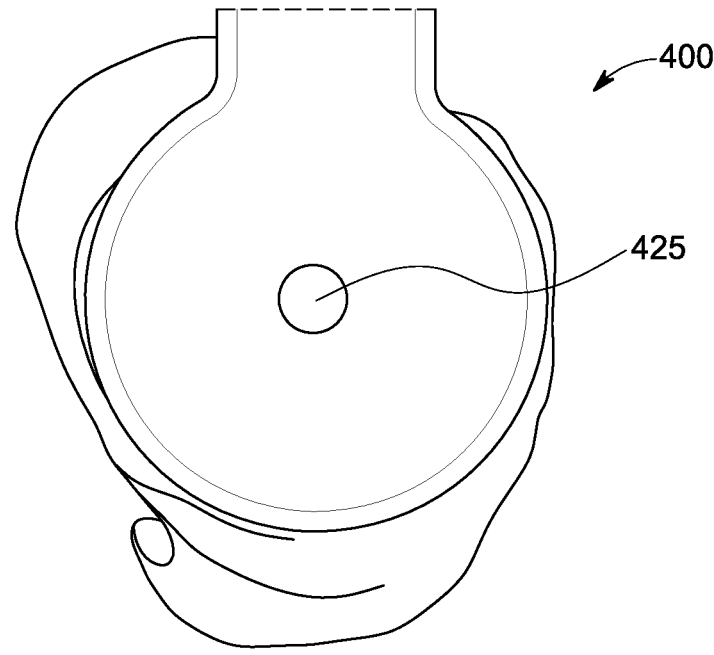

With reference to FIG. 28, the size of the toe implant assembly is determined. For example, after resection of the metatarsal head, the sizing device 400 (e.g., 14 mm, 16 mm, 18 mm, 20 mm, and 22 mm) may be placed over the resection and trialed until adequate coverage is fulfilled. The sizing device 400 desirably covers as much of the resected surface as possible with little to no overhang. For example, FIG. 29 illustrates an incorrect sized and positioned sizing device 400. FIG. 30 illustrates a correctly sized and positioned sizing device 400 as the sizer covers the cortical bone of the resection. The sizing device is aligned in its location where the implant is intended to be placed. The central hole 475 of the sizing device 400 establishes the central axis A (FIG. 28) of the implant and is desirably placed properly for appropriate implant function to occur.

Figure 31:
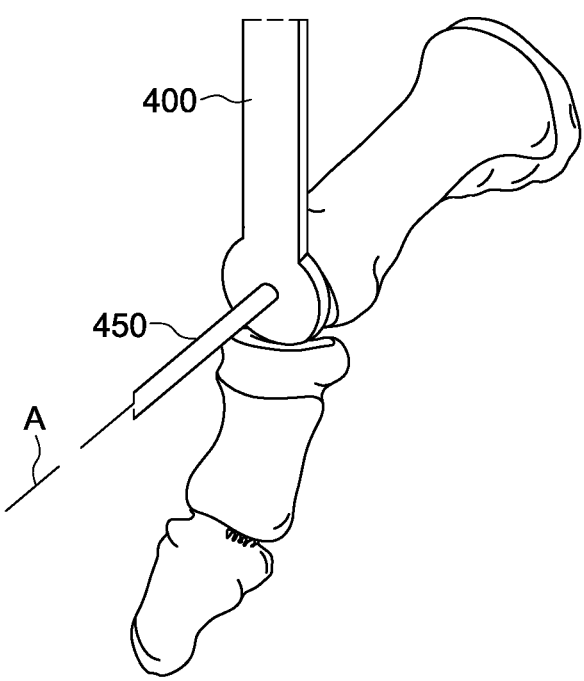

As shown in FIG. 31, after the appropriate toe implant assembly size has been selected, the sizing device 400 is checked to ensure it is flush against the resection surface and located in a proper location where adequate coverage is provided. While keeping the sizing device 400 in place, a pin 450 such as a 2 mm Steinman pin or Kirschner wire (K wire) is drilled through the central hole of the sizing device 400 along the normal axis. If the pin 450 is not established centrally along the normal axis, the pin 450 may be removed and repositioned until correct placement is achieved. C-Arm X-ray may be used to ensure pin is positioned along the normal axis.

Figure 32:
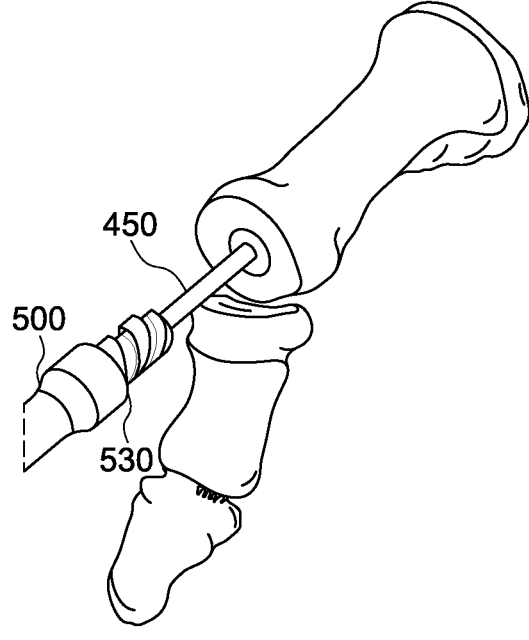
Figure 33:
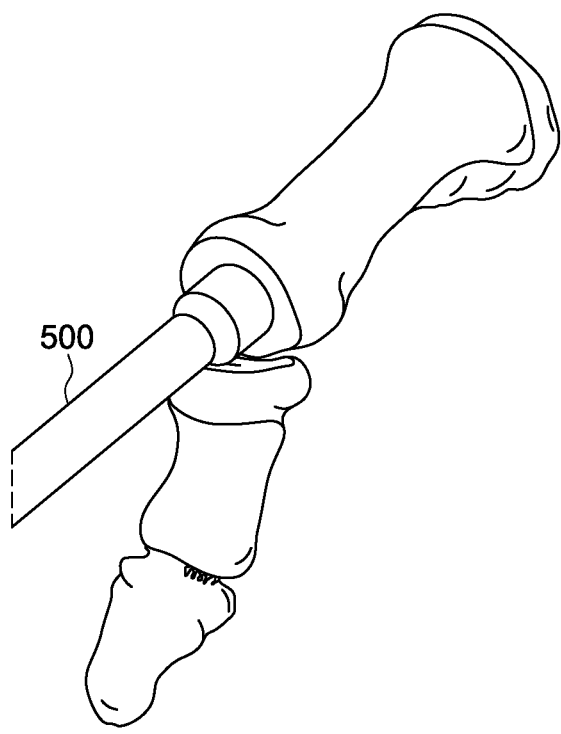

With reference to FIG. 32, the sizing device 400 (FIG. 31) is removed by sliding it over the top of the established pin 450. Once pin is positioned in an acceptable orientation, the appropriately sized cannulated drill or reamer 500 can be placed over the pin 450. Drilling is complete once the stop of the drill 500 contacts the resected planar surface of the resected bone as shown in FIG. 33. The size of the desired toe implant assembly will dictate which sized cannulated drill is utilized. A small, cannulated drill may be utilized with sizes 14 mm, 16 mm, and 18 mm sized toe implants assemblies. A large, cannulated drill may be utilized with the 20 mm and 22 mm sized toe implants assemblies.

Figure 34:
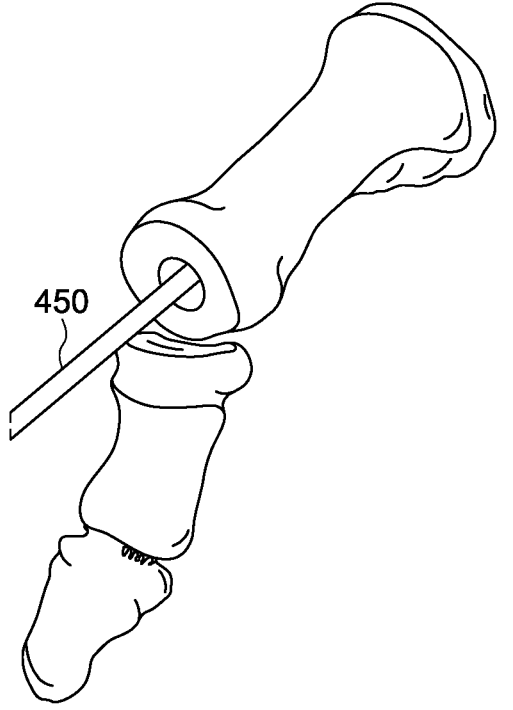
Figure 35:
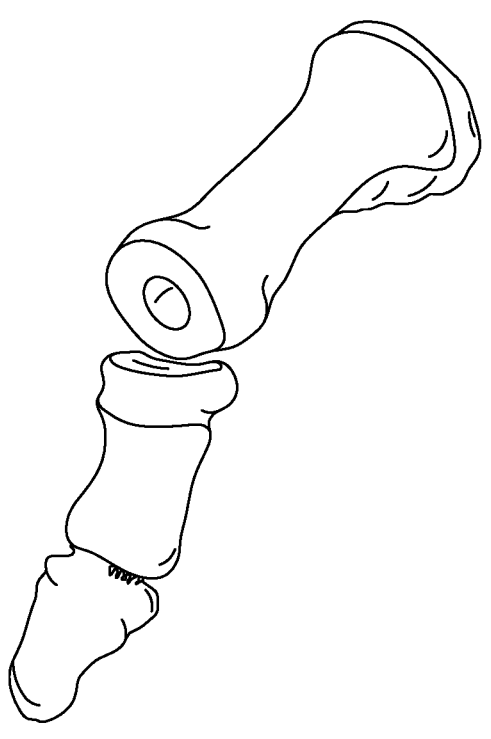

After drilling is completed, the cannulated drill or reamer 500 is removed as shown in FIG. 34, and then the cannulated pin 450 is removed as shown in FIG. 35.

Figure 36:
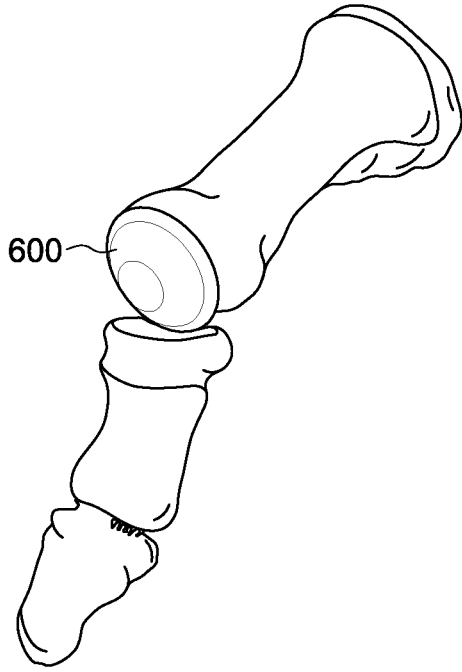

With reference to FIG. 36, the trialing device 600 that matches the desired tie implant assembly size is inserted to verify that the toe implant assembly size will be acceptable. Verification may include assessing for proper range of motion. If acceptable, the trialing device is then removed from the bone.

Figure 37:
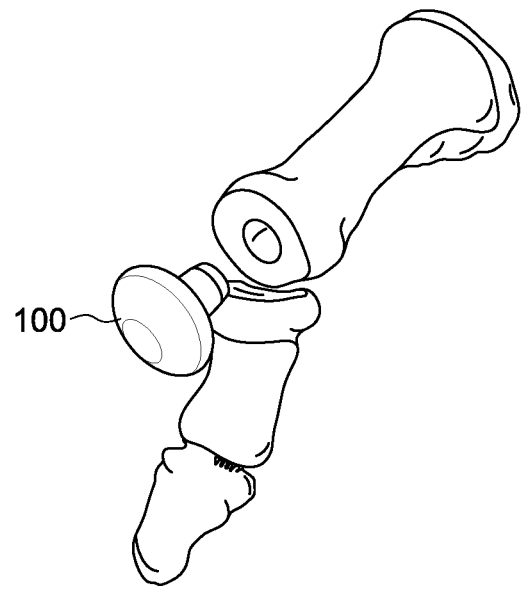

Thereafter, the toe implant assembly is installed. With reference to FIG. 37, the appropriately sized toe implant assembly 100 is removed from the packaging. Bone cement may be prepared per the manufacturer instructions and the prepared cement is introduced within the drilled hole and alongside the bottom of the toe implant assembly 100, ensuring no cement is placed on the articulation surface of the toe implant assembly.

Figure 38:
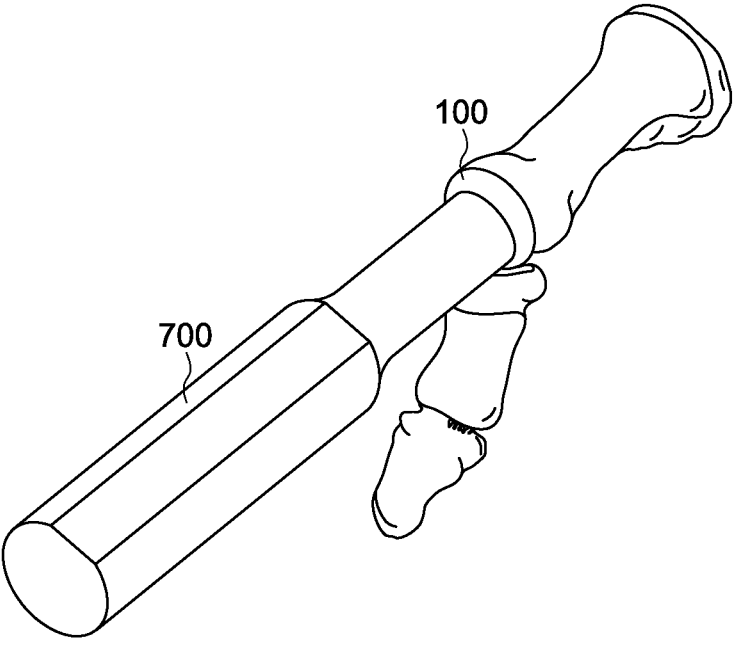
Figures 39, 40:
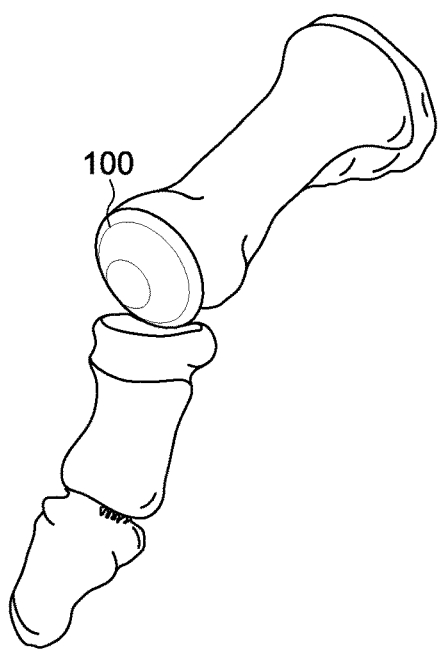

If bone cement is used, then after the bone cement has been applied, the tapered end of the toe implant assembly 100 is placed into the drilled hole in the bone. The concave surface of the tamping device 700 is placed against the articular surface of the toe implant assembly 100 and the tamping device 700 is progressively tapped with a mallet until the toe implant assembly 100 is firmly seated in the prepared site as shown in FIG. 38. Any extruded cement is removed with a curette, taking care not to scratch or scrape the toe implant assembly articular surface. To ensure the toe implant assembly is positioned properly, a surgeon may use their thumb to apply a force to the articulation surface to ensure that the toe implant assembly is well fixated and confirm that the toe implant assembly is fully seated against the resected bone as shown in FIG. 39. Rongeurs can be utilized to remove any excess or overhanging bone.

The method of manufacturing or fabrication of the toe implant assembly (See FIG. 43) may include, for example, forming a fixation member and molding, via compression, a polymer onto a top portion of the fixation member. Forming the fixation member may include, for example, machining a suitable material to the desired geometry. Additionally, forming the fixation member may include, for example, layering a plurality of porous sheets of titanium-based material and coupling the porous sheets to the fixation member. In other embodiments, the plurality of sheets may include tantalum-based structures, or other suitable material or materials. At least one sheet of the plurality of sheets may include, for example, a porous material. According to various embodiments, the porous portions of the fixation member may be sprayed or sinter-coated.

Molding, via compression, the polymer onto a top portion of the fixation member may also include, for example, applying heat to the polymer and applying pressure to the polymer. This method of manufacturing or fabrication may enable the polymer to flow to voids disposed by the dovetail channels the top portion of the fixation member.

As will be appreciated from the present discussion, the toe implant assembly is a hemiarthroplasty device that may operably restore the articular surface of the head of the first metatarsal bone in patients with degenerative and post-traumatic arthritis. The toe implant assemblies may be supplied in porous and non-porous variants with diameters of 14 mm, 16 mm, 18 mm, 20 mm, and 22 mm for selection by the physician. One toe implant assembly may be provided in sterile packaging.

The toe implant assembly may be implanted to replace the distal metatarsal surface of the great toe of patients with degenerative and post-traumatic arthritis in the first metatarsal joint in the presence of good bone stock along with the following clinical conditions: hallux valgus or hallux limitus, hallux rigidus, and an unstable or painful metatarsal/phalangeal (MTP) joint. The toe implant assembly may be a single use implant intended to be used with bone cement or used without bone cement.

As described above, a surgical technique may include a surgeon performing the following steps:
1. Incise and expose MTP joint;
2. Prepare the bone surface by resecting the distal head of metatarsal;
3. Determine appropriate implant size;
4. Place a central pin;
5. Drill the stem/prepare the bone cavity;
6. Remove pin;
7. Trial implant; and
8. Cement & Implant device.

The toe implant assembly may include a fixation member or stem that may be porous or non-porous, or a combination thereof. The porous stem variant may contain two subcomponents—a solid, grit blasted Ti-6Al-4V substrate and a porous, commercially pure titanium sleeve (OsteoSync® Ti material, Sites Medical, Inc.) that is wrapped and fusion bonded to the Ti-6Al-4V substrate. The bonded porous stem subcomponents become one monolithic stem component. The bottom of the stem is tapered to aid with insertion. The non-porous stem variant may include solid, grit blasted Ti-6Al-4V component that has "rib", or "barb" features to aid with insertion and initial fixation. The bottom of the stem is tapered to also aid with insertion. Both stem variants may have identical dove-tail channel features that serve as a mechanical locking mechanism between the stem and head components. The appropriate size articular head component is direct compression molded onto the appropriate size stem component. For each implant size, the stem component has a maximum diameter that is approximately 2 mm smaller than its corresponding head component. The toe implant assemblies may be made of ultra-high molecular weight polyethylene and crosslinked hyaluronan, and commercially pure titanium.

FIG. 40 illustrates a table with exterior toe implant assembly dimensions for the plurality of toe implant assemblies described above.

Figure 42:
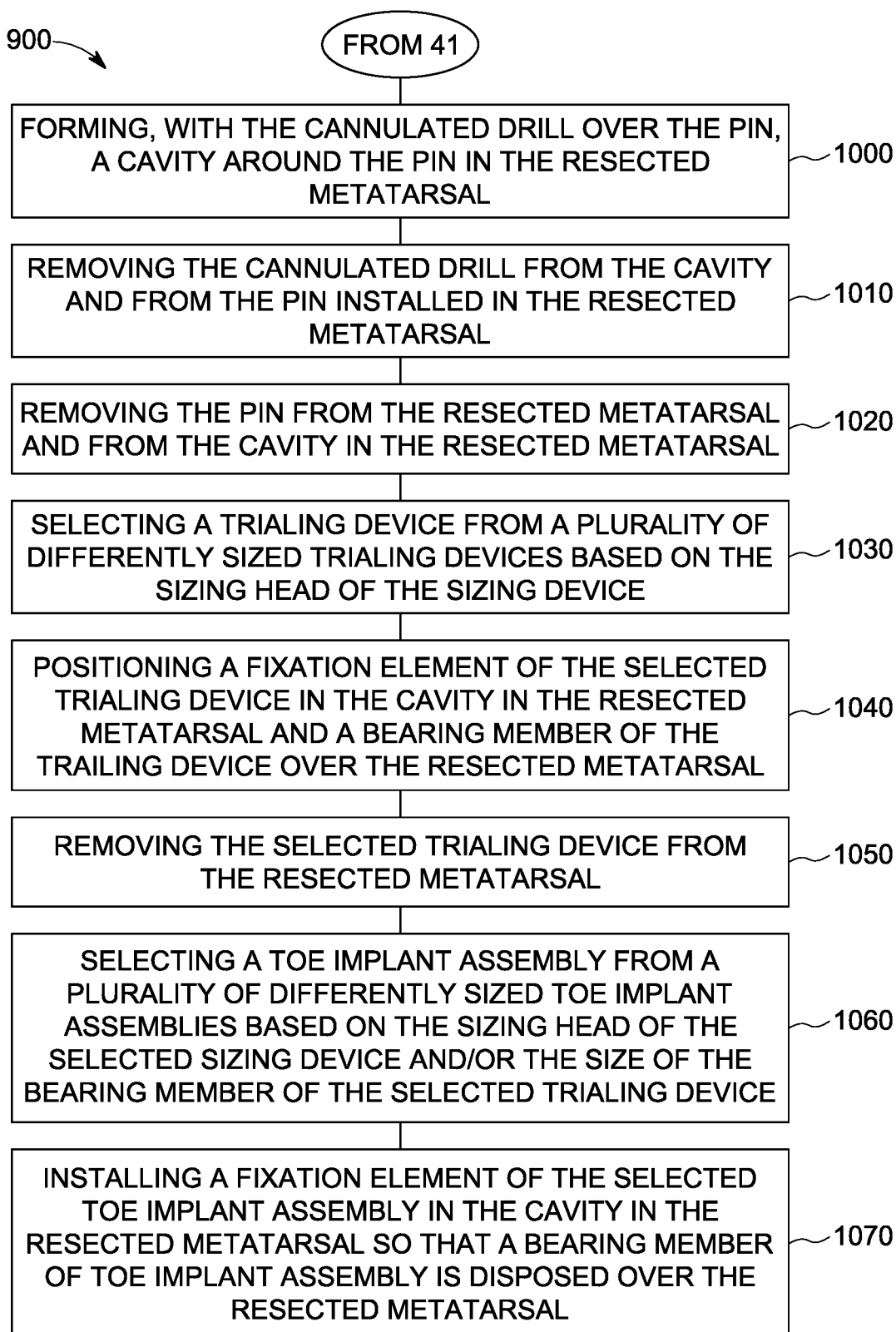

FIGS. 41 and 42 illustrate a surgical method 900, which includes for example, at 910 exposing a patient's metatarsophalangeal joint, at 920 resecting a distal head of metatarsal, at 930 selecting a sizing device from a plurality of differently sized sizing devices, at 940 positioning the selected sizing device having a sizing head over the resected distal end of the metatarsal, the sizing device having an aperture therethrough, at 950 confirming the sizing head of the selected sizing device conforms to the resected distal head of the metatarsal, at 960 positioning a pin through the aperture in the selected sizing device positioned over the resected distal head of the metatarsal, at 970 installing the pin into the metatarsal, at 980 removing the selected sizing device from the pin installed in the resected metatarsal, at 990 positioning a cannulated drill over the pin, at 1000 forming, with the cannulated drill over the pin, a cavity around the pin in the resected metatarsal, at 1010 removing the cannulated drill from the cavity and from the pin installed in the resected metatarsal, at 1020 removing the pin from the resected metatarsal and from the cavity in the resected metatarsal, at 1030 selecting a trialing device from a plurality of differently sized trialing devices based on the sizing head of the sizing device, at 1040 positioning a fixation member of the selected trialing device in the cavity in the resected metatarsal and a bearing member of the trialing device over the resected metatarsal, at 1050 removing the selected trialing device from the resected metatarsal, at 1060 selecting a toe implant assembly from a plurality of differently sized toe implant assemblies based on the sizing head of the selected sizing device and/or the size of the bearing member of the selected trialing device, and at 1070 installing a fixation member of the selected toe implant assembly in the cavity in the resected metatarsal so that a bearing member of the toe implant assembly is disposed over the resected metatarsal.

FIG. 43 illustrates a method 1100 of manufacturing a toe implant, which includes, for example, at 1110 forming a fixation member having a platform portion and fixation portion, the platform having a peripheral portion, and at 1120 molding a polymer onto the platform portion of the fixation member, the molded polymer having a peripheral portion that extends outward from the peripheral portion of the platform.

Figure 44:
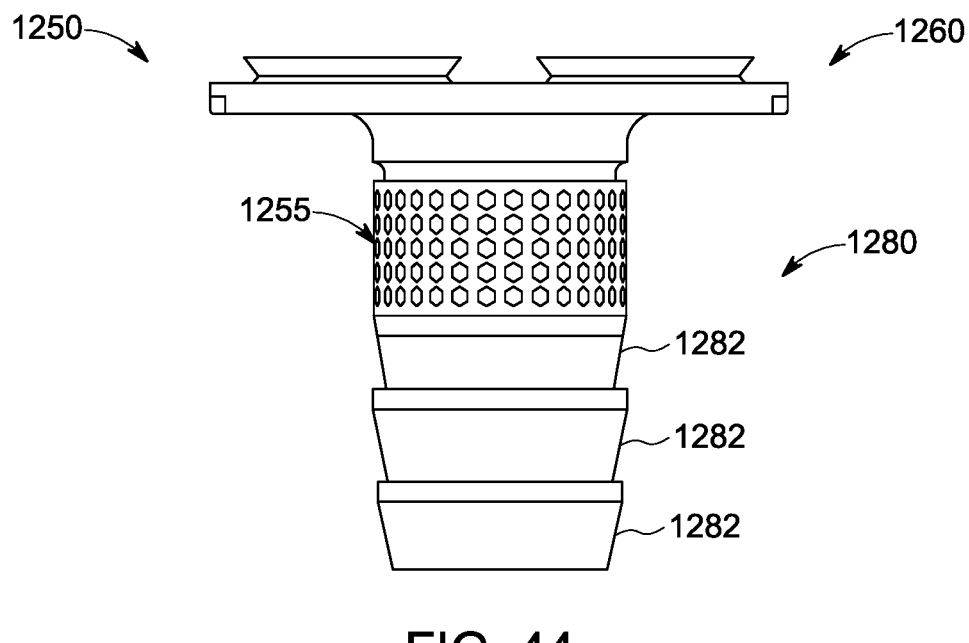
FIG. 44 is a side elevational view of a fixation member for a toe implant assembly, according to an embodiment of the present disclosure.

FIG. 44 illustrates a fixation member 1250 attachable or couplable to an articulating or bearing member such as any of those disclosed herein to form a toe implant assembly, according to an embodiment of the present disclosure. The fixation member 1250 may include a cylindrical platform portion 1260 and a fixation portion 1280. The platform portion 1260 may be essentially the same as the platform member 160 (FIG. 9) of fixation member 150 (FIG. 9).

In this illustrated embodiment, the fixation portion 1280 may include a plurality or series of tapered cylindrical sections 1282 and a cylindrical support portion (not shown in FIG. 44) over which is disposed a porous sleeve 1255. The tapered cylindrical sections 1282 may be essentially the same as a portion of the plurality or series of tapered cylindrical sections 182 (FIG. 9) of fixation member 150 (FIG. 9). The porous sleeve 1255 may be essentially the same as porous sleeve 255 (FIG. 14) of fixation member 250 (FIG. 14). For example, the porous sleeve 1255 may extend over a smaller portion of the fixation portion 1280 compared to the fixation portion 280 (FIG. 14) of the fixation member 250 (FIG. 14).

Figure 45:
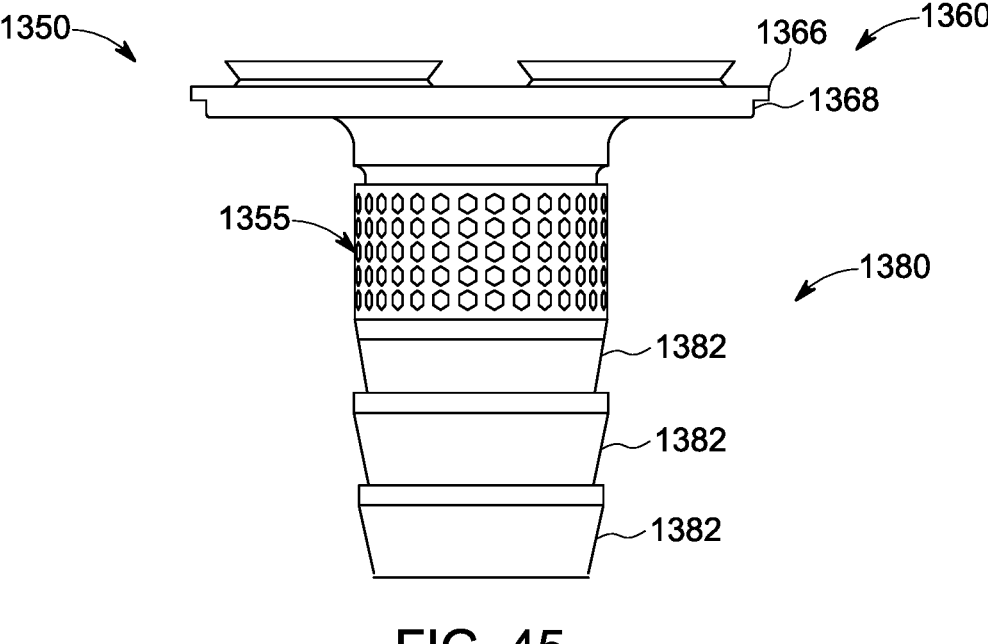
FIG. 45 is a side elevational view of a fixation member for a toe implant assembly, according to an embodiment of the present disclosure.

FIG. 45 illustrate a fixation member 1350 attachable or couplable to an articulating or bearing member such as any of those disclosed herein to form a toe implant assembly, according to an embodiment of the present disclosure. The fixation member 1350 may include a cylindrical platform portion 1360 and a fixation portion 1380. The platform member 1360 may be essentially the same as the platform portion 360 (FIG. 16) of fixation member 350 (FIG. 16). For example, the cylindrical platform portion 1360 may include a first upper platform portion 1366 and a second lower platform portion 1368, e.g., the platform may include two separate cylindrical platforms or portions having different peripheral portions or diameters.

In this illustrated embodiment, the fixation portion 1380 may include a plurality or series of tapered cylindrical sections 1382 and a cylindrical support portion (not shown in FIG. 45) over which is disposed a porous sleeve 1355. The tapered cylindrical sections 1382 may be essentially the same as a portion of the plurality or series of tapered cylindrical sections 182 (FIG. 9) of fixation member 150 (FIG. 9). The porous sleeve 1355 may be essentially the same as porous sleeve 255 (FIG. 14) of fixation member 250 (FIG. 14). For example, the porous sleeve 1355 may extend over a smaller portion of the fixation portion 1380 compared to the fixation portion 280 (FIG. 14) of the fixation member 250 (FIG. 14).

Figure 46:
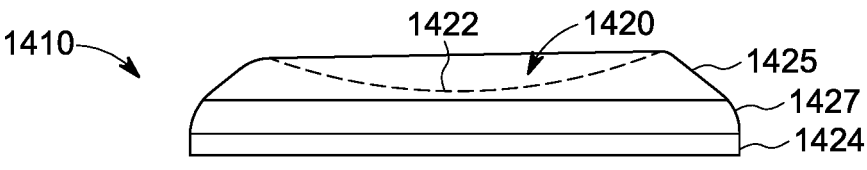
FIG. 46 is a side elevational view of an articulating or bearing member having a concave articulating surface for a toe implant assembly, according to an embodiment of the present disclosure.

FIG. 46 illustrates an articulating or bearing member 1410 having a concave interface surface 1420 attachable or couplable to a fixation member such as any of those disclosed herein to form a toe implant assembly, according to an embodiment of the present disclosure.

The curved interface surface 1420 of the bearing member 1410 may be designed to replicate, for example, the normal anatomy of a base of a patient's proximal phalanges. The curved interface surface 1420 may include a non-constant curved surface 1422, for example, or maybe a constant radial surface similar to an outer portion of a sphere. The curved interface surface 1420 of the bearing member 1410 may be, for example, generally concave. Additionally, the bearing member 1410 may include, for example, a second surface 1424 that is generally cylindrical and may be commensurate or larger in diameter than the cylindrical platform portion of the fixation member. The curved interface surface 1420 may include, for example, an upper curved edge 1425 and a lower curved edge 1427. Further, the lower curved edge 1427 may be joined to the upper curved edge 1425 and commensurate in diameter with the second surface 1424. Additionally, the bearing member 1410 may be designed to correspond to a diameter of a corresponding sizing device. The bearing member 1410 may be designed in multiple sizes to allow for the selection by a medical professional based on the width and/or length of the particular bone being treated. For example, in some embodiments, the articulating or bearing member 1410 may be configured to correspond to the dimensions illustrated in FIG. 40.

Figure 47:
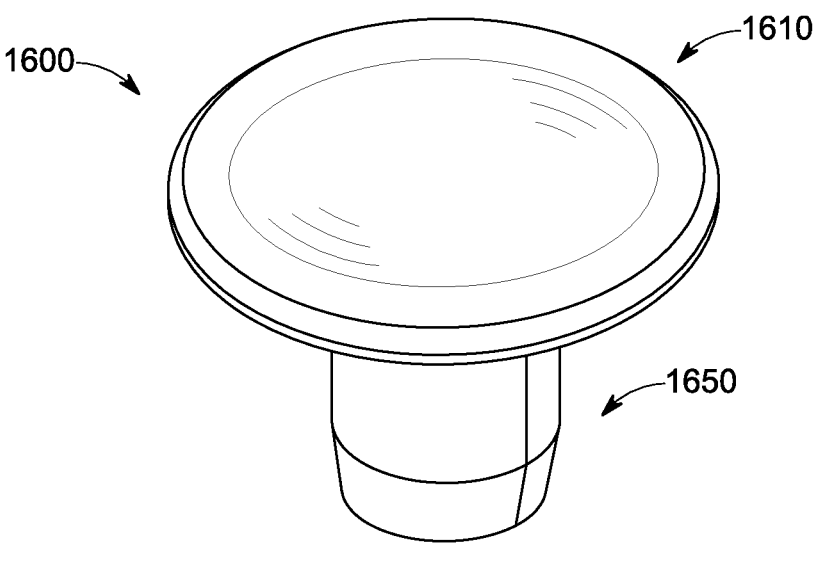
FIG. 47 is a top perspective view of a trialing device having a concave articulating surface, according to an embodiment of the present disclosure.

With reference to FIG. 47, a kit may include a trialing device 1600 having a simulated bearing member 1610 configured to engage and be positioned on, for example, a resected base of a patient's proximal phalanx, and a simulated fixation member 1650 configure to engage the cavity in the drilled phalanx bone. The trialing device 1600 may be sized to correspond to a corresponding bearing member and fixation member of a toe implant assembly. Additionally, the trialing device 1600 may be designed to correspond to a diameter of a corresponding sizing device. The trialing device 1600 may be designed in multiple sizes to allow for the selection by a medical professional based on the width and/or length of the particular bone being treated.

Figure 48:
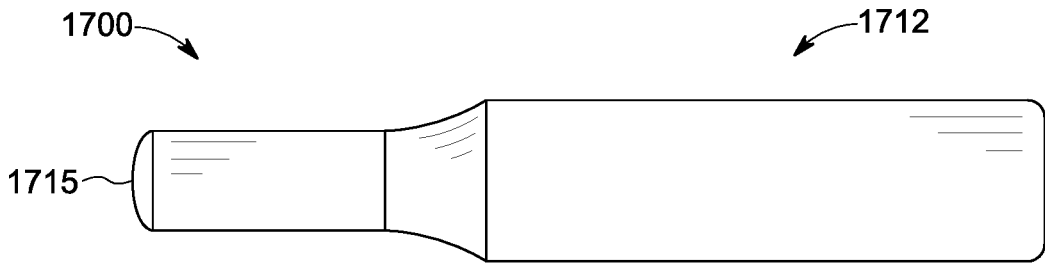
FIG. 48 is a side elevational view of a tamping device, according to an embodiment of the present disclosure.

As shown in FIG. 48, the kit may include a tamping device 1700 having an elongated body 1712 with a convex surface 1715 at one end. The convex surface 1715 is configured to engage a bearing member of a toe implant assembly. The tamping device 1700 may be sized to correspond to the curvature of the bearing member of the toe implant assembly.

A surgical method for replacing a portion of a human toe joint may include toe implant assemblies incorporating any of the disclosed fixation members, and the bearing member 1410 (FIG. 46) using the trialing device 1600 (FIG. 47) and tamping device 1700 (FIG. 48), in a similar process as disclosed in the surgical method illustrated in FIGS. 25-39, according to an embodiment of the present disclosure.

As may be recognized by those of ordinary skill in the art based on the teachings herein, numerous changes and modifications may be made to the above-described and other embodiments of the present disclosure without departing from the scope of the disclosure. The implants, screws, and other components of the devices and/or apparatus as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and apparatus may include more or fewer components or features than the embodiments as described and illustrated herein. Accordingly, this detailed description of the currently-preferred embodiments is to be taken as illustrative, as opposed to limiting the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The present disclosure has been described with reference to the preferred embodiments. It will be understood that the architectural and operational embodiments described herein are exemplary of a plurality of possible arrangements to provide the same general features, characteristics, and general apparatus operation. Modifications and alterations will occur to others upon a reading and understanding of the preceding detailed description. It is intended that the present disclosure be construed as including all such modifications and alterations.

What is claimed is:

1. A toe implant assembly comprising:
a bearing member having a curved interface surface and a peripheral portion; and
a fixation member having a platform portion and fixation portion, the platform portion having a peripheral portion sized smaller than the peripheral portion of the bearing member;
the fixation member being coupled to the bearing member so that the peripheral portion of the bearing member extends outwardly from the peripheral portion of the platform portion;
the fixation portion comprising four raised portions, the raise portions defining four crisscrossed dovetail channels;
the bearing member comprising an integrally attached coupling portion, wherein the coupling portion of the bearing member includes four crisscrossed integrally attached raised coupling sections; and
wherein each one of the four coupling sections are configured to fit into a respective one of the dovetail channels to prevent translational movement of the bearing member relative to the fixation member.

2. The toe implant assembly of claim 1, wherein the fixation portion comprises a series of tapered cylindrical sections, wherein outer diameters of each cylindrical section are progressively smaller so that the fixation portion tapers from a bottom of the bearing member to a distal end of the fixation portion.

3. The toe implant assembly of claim 2, wherein each of the series of tapered cylindrical sections comprise an angled surface to facilitate insertion of the fixation portion into a bone.

4. The toe implant assembly of claim 1, wherein the fixation portion comprises an outer porous surface.

5. The toe implant assembly of claim 4, wherein the fixation portion comprises a hollow sleeve defining the outer porous surface.

6. The toe implant assembly of claim 4, wherein:
the platform portion of the fixation member comprises a first platform portion having a first peripheral portion and a second platform portion having a second peripheral portion sized less than the first peripheral portion, and
the peripheral portion of the bearing member extends around the platform portion of the fixation member with the first peripheral portion of the first platform being sandwiched therebetween.

7. The toe implant assembly of claim 1, wherein the bearing member comprises a periphery have a diameter between 14 mm and 22 mm.

8. The toe implant assembly of claim 1, wherein the bearing member comprises a polymer material, and the fixation member comprises a biocompatible metal.

9. The toe implant assembly of claim 1, wherein the curved interface surface comprises at least one of a concave surface and a convex surface.

10. The toe implant assembly of claim 1, wherein the fixation member comprises an end portion having an angular outer surface capable of preventing subsidence of the toe implant assembly into a patient's bone.

11. The toe implant assembly of claim 1, wherein the fixation member further comprises a distal tapered cylindrical portion, wherein the distal tapered cylindrical portion has an angular surface for facilitating a clearance when the toe implant assembly is inserted into the bone.

12. The toe implant assembly of claim 1, wherein the platform portion and the fixation portion are integrally connected to each other.

13. The toe implant assembly of claim 12, wherein the fixation portion comprises a proximal end and a distal end, wherein the platform portion and fixation portion are coupled together at the proximal end.

14. The toe implant assembly of claim 1, wherein the four raised portions extend a set distance from a proximal surface of the platform portion of the fixation member to facilitate the coupling of the bearing member to the fixation member.

* * * * *